United States Patent
Davare

(10) Patent No.: US 10,100,366 B2
(45) Date of Patent: Oct. 16, 2018

(54) METHODS OF DETECTING CANCERS SENSITIVE TO CABOZANTINIB

(71) Applicant: Monika A. Davare, Portland, OR (US)

(72) Inventor: Monika A. Davare, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 15/356,133

(22) Filed: Nov. 18, 2016

(65) Prior Publication Data

US 2017/0145517 A1      May 25, 2017

Related U.S. Application Data

(60) Provisional application No. 62/258,168, filed on Nov. 20, 2015.

(51) Int. Cl.
*C12Q 1/68* (2018.01)
*A61K 31/47* (2006.01)
*C12Q 1/6886* (2018.01)

(52) U.S. Cl.
CPC ............ *C12Q 1/6886* (2013.01); *A61K 31/47* (2013.01); *C12Q 2600/106* (2013.01); *C12Q 2600/156* (2013.01)

(58) Field of Classification Search
CPC .................. A61K 31/47; C12Q 1/6886; C12Q 2600/156; C12Q 2600/106
See application file for complete search history.

(56) References Cited

FOREIGN PATENT DOCUMENTS

WO    WO 2014152777 A2 *   9/2014   ........... C12Q 1/6886

OTHER PUBLICATIONS

Katayama et al (Clinical Cancer Research, 2014).*

* cited by examiner

*Primary Examiner* — Kortney L. Klinkel
*Assistant Examiner* — Ibrahim D Bori

(57) ABSTRACT

The emergence of resistance to targeted therapy is a recurrent clinical challenge and requires development and validation of secondary agents with improved activity. Accompanied by experimental cell-based and structural validation, this report of a near complete response to cabozantinib in a ROS1-rearranged lung adenocarcinoma patient with acquired resistance to crizotinib mediated by a novel CD74-ROS1 D2033N solvent-front mutation provides the first clinical example of crizotinib resistance overcome by targeted therapy in a ROS1-rearranged malignancy.

11 Claims, 13 Drawing Sheets
Specification includes a Sequence Listing.

|  |  | | | |
|---|---|---|---|---|
| ROS1 | 2029 | MEGG LLTY | 2037 |

ROS1 paralogs:
| ALK | 1199 | MAGG LKSF | 1207 |
| DDR1 | 704 | MENG LNQF | 712 |
| DDR2 | 857 | MENG LNQF | 865 |
| IGF1R | 1092 | MTRG LKSY | 1100 |
| INSR | 1106 | MAHG LKSY | 1114 |
| INSRR | 1062 | MTRG LKSH | 1070 |
| LTK | 593 | MSGG MKSF | 601 |
| MUSK | 858 | MAYG LNEF | 866 |
| NTRK1 | 592 | MRHG LNRF | 600 |
| NTRK2 | 620 | MKHG LNKF | 628 |
| NTRK3 | 620 | MKHG LNKF | 628 |
| ROR1 | 555 | INQG LHEF | 563 |
| ROR2 | 556 | CSHG LHEF | 564 |

Additional kinases:
| ABL1 | 318 | MTYGNLLDY | 326 |
| BRAF | 531 | WCEGSSLYH | 539 |
| EGFR | 793 | MPFGCLLDY | 801 |
| MET | 1160 | MKHG LRNF | 1168 |
| RET | 807 | AKYGSLRGF | 815 |
| SRC | 344 | MSKGSLLDF | 352 |

| IC$_{50}$ (nM) | Wildtype | D2033N |
|---|---|---|
| Crizotinib | 14.93 | 140.1 |
| Cabozantinib | 4.574 | 0.6492 |
| Foretinib | 4.239 | 2.188 |
| Ceritinib | 70.33 | 305.8 |
| Brigatinib | 18.63 | 69.11 |
| PF-06463922 | 0.05339 | 0.3759 |

Figure 9

| | Clinical Course | Pathologic Testing |
|---|---|---|
| February 2011 - March 2011 | A 50 year-old Asian female never smoker with no significant past medical history presented with increasing cough, dyspnea, and fevers. Chest x-ray revealed a right-sided pleural effusion. A thoracentesis and subsequent video-assisted thoracoscopy (VATS) and talc pleurodesis were performed. | Thoracentesis (February 2011): Cytology was positive for cells consistent with metastatic adenocarcinoma.<br>Parietal pleural biopsy (March 2011): Metastatic adenocarcinoma with a solid growth pattern consistent with a lung primary was identified. Immunohistochemistry was positive for TTF-1.<br>Molecular profiling: Initial testing of the pleural biopsy (EGFR sizing assay for indels, multiplex mass-spectrometry / Sequenom for 91 point mutations in EGFR, ERBB2, KRAS, NRAS, BRAF, MAP2K1, PIK3CA, and AKT1, and FISH for ALK rearrangement and MET amplification) did not detect a genomic alteration. |
| March 2011 - January 2012 | The patient received first-line systemic therapy with cisplatin, pemetrexed, and bevacizumab for 3 cycles. A durable partial response to therapy was noted. Cisplatin subsequently discontinued secondary to persistent nausea despite maximal supportive care and maintenance pemetrexed and bevacizumab was initiated for a total of 9 cycles. | |
| February 2012 - August 2012 | Maintenance therapy with pemetrexed and bevacizumab was discontinued due to increasing fatigue. The patient was thereafter placed on active observation. | Molecular profiling: Testing of the same pleural biopsy from March 2011 was performed. RET break-apart FISH was negative; however, ROS1 FISH was positive for a ROS1 rearrangement. Broad, hybrid-capture next-generation sequencing (MSK-IMPACT, Illumina HiSeq 2500(3)) confirmed the presence of a CD74-ROS1 fusion. |
| September 2012 - November 2014 | The patient was treated with crizotinib, initially dosed at 250 mg twice daily. A durable, confirmed partial response achieved (best objective response of 64% disease reduction, RECIST v1.1(4)). New brain metastases were noted in February 2014. Whole brain radiation administered in March 2014. Disease burden outside the brain remained stable on crizotinib. The patient thus continued crizotinib until November 2014 with continued disease control. | |
| December 2014 - ongoing | Widespread disease progression on continued crizotinib therapy was noted. Imaging revealed bilateral new and enlarging pulmonary nodules, increasing mediastinal and retroperitoneal adenopathy, and increasing peritoneal carcinomatosis. The patient was enrolled onto a phase II clinical trial of the ROS1 inhibitor cabozantinib (NCT01639508). Cabozantinib was initially dosed at 60 mg daily. Within a few days, the patient developed a dramatic clinical response with a decrease in abdominal discomfort and cough that were worsening prior to cabozantinib therapy. A confirmed partial response was achieved with a best objective response of 92% disease reduction. The patient remains on therapy 10 months into treatment and remains clinically well. | Retroperitoneal lymph node biopsy (December 2014): To investigate potential mechanisms of acquired resistance, a biopsy of a growing retroperitoneal lymph node was performed. Metastatic adenocarcinoma morphologically similar to the patient's pleural biopsy was noted on pathologic review. Immunohistochemistry was positive for TTF-1.<br>Molecular profiling: Broad, hybrid-capture next-generation sequencing of tumor from the retroperitoneal lymph node was performed and compared to sequencing of the patient's pre-crizotinib pleural biopsy from March 2011. This confirmed the persistence of CD74-ROS1 in the post-crizotinib treatment sample, and detected an acquired $CD74\text{-}ROS1^{D2033N}$ mutation that was not present prior to crizotinib therapy. |

SEQUENCE LISTING

```
<160> NUMBER OF SEQ ID NOS: 3

<210> SEQ ID NO 1
<211> LENGTH: 2347
<212> TYPE: PRT
<213> ORGANISM: Homo sapiens

<400> SEQUENCE: 1

Met Lys Asn Ile Tyr Cys Leu Ile Pro Lys Leu Val Asn Phe Ala Thr
1               5                   10                  15

Leu Gly Cys Leu Trp Ile Ser Val Val Gln Cys Thr Val Leu Asn Ser
            20                  25                  30

Cys Leu Lys Ser Cys Val Thr Asn Leu Gly Gln Gln Leu Asp Leu Gly
        35                  40                  45

Thr Pro His Asn Leu Ser Glu Pro Cys Ile Gln Gly Cys His Phe Trp
```

```
            50                  55                  60
Asn Ser Val Asp Gln Lys Asn Cys Ala Leu Lys Cys Arg Glu Ser Cys
 65                  70                  75                  80
Glu Val Gly Cys Ser Ser Ala Glu Gly Ala Tyr Glu Glu Val Leu
                 85                  90                  95
Glu Asn Ala Asp Leu Pro Thr Ala Pro Phe Ala Ser Ser Ile Gly Ser
                100                 105                 110
His Asn Met Thr Leu Arg Trp Lys Ser Ala Asn Phe Ser Gly Val Lys
                115                 120                 125
Tyr Ile Ile Gln Trp Lys Tyr Ala Gln Leu Leu Gly Ser Trp Thr Tyr
                130                 135                 140
Thr Lys Thr Val Ser Arg Pro Ser Tyr Val Val Lys Pro Leu His Pro
145                 150                 155                 160
Phe Thr Glu Tyr Ile Phe Arg Val Val Trp Ile Phe Thr Ala Gln Leu
                165                 170                 175
Gln Leu Tyr Ser Pro Pro Ser Pro Ser Tyr Arg Thr His Pro His Gly
                180                 185                 190
Val Pro Glu Thr Ala Pro Leu Ile Arg Asn Ile Glu Ser Ser Ser Pro
                195                 200                 205
Asp Thr Val Glu Val Ser Trp Asp Pro Pro Gln Phe Pro Gly Gly Pro
210                 215                 220
Ile Leu Gly Tyr Asn Leu Arg Leu Ile Ser Lys Asn Gln Lys Leu Asp
225                 230                 235                 240
Ala Gly Thr Gln Arg Thr Ser Phe Gln Phe Tyr Ser Thr Leu Pro Asn
                245                 250                 255
Thr Ile Tyr Arg Phe Ser Ile Ala Ala Val Asn Glu Val Gly Glu Gly
                260                 265                 270
Pro Glu Ala Glu Ser Ser Ile Thr Thr Ser Ser Ala Val Gln Gln
                275                 280                 285
Glu Glu Gln Trp Leu Phe Leu Ser Arg Lys Thr Ser Leu Arg Lys Arg
                290                 295                 300
Ser Leu Lys His Leu Val Asp Glu Ala His Cys Leu Arg Leu Asp Ala
305                 310                 315                 320
Ile Tyr His Asn Ile Thr Gly Ile Ser Val Asp Val His Gln Gln Ile
                325                 330                 335
Val Tyr Phe Ser Glu Gly Thr Leu Ile Trp Ala Lys Lys Ala Ala Asn
                340                 345                 350
Met Ser Asp Val Ser Asp Leu Arg Ile Phe Tyr Arg Gly Ser Gly Leu
                355                 360                 365
Ile Ser Ser Ile Ser Ile Asp Trp Leu Tyr Gln Arg Met Tyr Phe Ile
                370                 375                 380
Met Asp Glu Leu Val Cys Val Cys Asp Leu Glu Asn Cys Ser Asn Ile
385                 390                 395                 400
Glu Glu Ile Thr Pro Pro Ser Ile Ser Ala Pro Gln Lys Ile Val Ala
                405                 410                 415
Asp Ser Tyr Asn Gly Tyr Val Phe Tyr Leu Leu Arg Asp Gly Ile Tyr
                420                 425                 430
Arg Ala Asp Leu Pro Val Pro Ser Gly Arg Cys Ala Glu Ala Val Arg
                435                 440                 445
Ile Val Glu Ser Cys Thr Leu Lys Asp Phe Ala Ile Lys Pro Gln Ala
                450                 455                 460
Lys Arg Ile Ile Tyr Phe Asn Asp Thr Ala Gln Val Phe Met Ser Thr
465                 470                 475                 480
```

-continued

Phe Leu Asp Gly Ser Ala Ser His Leu Ile Leu Pro Arg Ile Pro Phe
            485                 490                 495

Ala Asp Val Lys Ser Phe Ala Cys Glu Asn Asn Asp Phe Leu Val Thr
            500                 505                 510

Asp Gly Lys Val Ile Phe Gln Gln Asp Ala Leu Ser Phe Asn Glu Phe
            515                 520                 525

Ile Val Gly Cys Asp Leu Ser His Ile Glu Glu Phe Gly Phe Gly Asn
            530                 535                 540

Leu Val Ile Phe Gly Ser Ser Gln Leu His Pro Leu Pro Gly Arg
545                 550                 555                 560

Pro Gln Glu Leu Ser Val Leu Phe Gly Ser His Gln Ala Leu Val Gln
            565                 570                 575

Trp Lys Pro Pro Ala Leu Ala Ile Gly Ala Asn Val Ile Leu Ile Ser
            580                 585                 590

Asp Ile Ile Glu Leu Phe Glu Leu Gly Pro Ser Ala Trp Gln Asn Trp
            595                 600                 605

Thr Tyr Glu Val Lys Val Ser Thr Gln Asp Pro Pro Glu Val Thr His
            610                 615                 620

Ile Phe Leu Asn Ile Ser Gly Thr Met Leu Asn Val Pro Glu Leu Gln
625                 630                 635                 640

Ser Ala Met Lys Tyr Lys Val Ser Val Arg Ala Ser Ser Pro Lys Arg
            645                 650                 655

Pro Gly Pro Trp Ser Glu Pro Ser Val Gly Thr Thr Leu Val Pro Ala
            660                 665                 670

Ser Glu Pro Pro Phe Ile Met Ala Val Lys Glu Asp Gly Leu Trp Ser
            675                 680                 685

Lys Pro Leu Asn Ser Phe Gly Pro Gly Glu Phe Leu Ser Ser Asp Ile
            690                 695                 700

Gly Asn Val Ser Asp Met Asp Trp Tyr Asn Asn Ser Leu Tyr Tyr Ser
705                 710                 715                 720

Asp Thr Lys Gly Asp Val Phe Val Trp Leu Leu Asn Gly Thr Asp Ile
            725                 730                 735

Ser Glu Asn Tyr His Leu Pro Ser Ile Ala Gly Ala Gly Ala Leu Ala
            740                 745                 750

Phe Glu Trp Leu Gly His Phe Leu Tyr Trp Ala Gly Lys Thr Tyr Val
            755                 760                 765

Ile Gln Arg Gln Ser Val Leu Thr Gly His Thr Asp Ile Val Thr His
            770                 775                 780

Val Lys Leu Leu Val Asn Asp Met Val Val Asp Ser Val Gly Gly Tyr
785                 790                 795                 800

Leu Tyr Trp Thr Thr Leu Tyr Ser Val Glu Ser Thr Arg Leu Asn Gly
            805                 810                 815

Glu Ser Ser Leu Val Leu Gln Thr Gln Pro Trp Phe Ser Gly Lys Lys
            820                 825                 830

Val Ile Ala Leu Thr Leu Asp Leu Ser Asp Gly Leu Leu Tyr Trp Leu
            835                 840                 845

Val Gln Asp Ser Gln Cys Ile His Leu Tyr Thr Ala Val Leu Arg Gly
            850                 855                 860

Gln Ser Thr Gly Asp Thr Thr Ile Thr Glu Phe Ala Ala Trp Ser Thr
865                 870                 875                 880

Ser Glu Ile Ser Gln Asn Ala Leu Met Tyr Tyr Ser Gly Arg Leu Phe
            885                 890                 895

Trp Ile Asn Gly Phe Arg Ile Ile Thr Thr Gln Glu Ile Gly Gln Lys
                900                 905                 910

Thr Ser Val Ser Val Leu Glu Pro Ala Arg Phe Asn Gln Phe Thr Ile
        915                 920                 925

Ile Gln Thr Ser Leu Lys Pro Leu Pro Gly Asn Phe Ser Phe Thr Pro
        930                 935                 940

Lys Val Ile Pro Asp Ser Val Gln Glu Ser Ser Phe Arg Ile Glu Gly
945                 950                 955                 960

Asn Ala Ser Ser Phe Gln Ile Leu Trp Asn Gly Pro Pro Ala Val Asp
                965                 970                 975

Trp Gly Val Val Phe Tyr Ser Val Glu Phe Ser Ala His Ser Lys Phe
        980                 985                 990

Leu Ala Ser Glu Gln His Ser Leu Pro Val Phe Thr Val Glu Gly Leu
        995                 1000                1005

Glu Pro Tyr Ala Leu Phe Asn Leu Ser Val Thr Pro Tyr Thr Tyr
    1010                1015                1020

Trp Gly Lys Gly Pro Lys Thr Ser Leu Ser Leu Arg Ala Pro Glu
    1025                1030                1035

Thr Val Pro Ser Ala Pro Glu Asn Pro Arg Ile Phe Ile Leu Pro
    1040                1045                1050

Ser Gly Lys Cys Cys Asn Lys Asn Glu Val Val Val Glu Phe Arg
    1055                1060                1065

Trp Asn Lys Pro Lys His Glu Asn Gly Val Leu Thr Lys Phe Glu
    1070                1075                1080

Ile Phe Tyr Asn Ile Ser Asn Gln Ser Ile Thr Asn Lys Thr Cys
    1085                1090                1095

Glu Asp Trp Ile Ala Val Asn Val Thr Pro Ser Val Met Ser Phe
    1100                1105                1110

Gln Leu Glu Gly Met Ser Pro Arg Cys Phe Ile Ala Phe Gln Val
    1115                1120                1125

Arg Ala Phe Thr Ser Lys Gly Pro Gly Pro Tyr Ala Asp Val Val
    1130                1135                1140

Lys Ser Thr Thr Ser Glu Ile Asn Pro Phe Pro His Leu Ile Thr
    1145                1150                1155

Leu Leu Gly Asn Lys Ile Val Phe Leu Asp Met Asp Gln Asn Gln
    1160                1165                1170

Val Val Trp Thr Phe Ser Ala Glu Arg Val Ile Ser Ala Val Cys
    1175                1180                1185

Tyr Thr Ala Asp Asn Glu Met Gly Tyr Tyr Ala Glu Gly Asp Ser
    1190                1195                1200

Leu Phe Leu Leu His Leu His Asn Arg Ser Ser Ser Glu Leu Phe
    1205                1210                1215

Gln Asp Ser Leu Val Phe Asp Ile Thr Val Ile Thr Ile Asp Trp
    1220                1225                1230

Ile Ser Arg His Leu Tyr Phe Ala Leu Lys Glu Ser Gln Asn Gly
    1235                1240                1245

Met Gln Val Phe Asp Val Asp Leu Glu His Lys Val Lys Tyr Pro
    1250                1255                1260

Arg Glu Val Lys Ile His Asn Arg Asn Ser Thr Ile Ile Ser Phe
    1265                1270                1275

Ser Val Tyr Pro Leu Leu Ser Arg Leu Tyr Trp Thr Glu Val Ser
    1280                1285                1290

Asn Phe Gly Tyr Gln Met Phe Tyr Tyr Ser Ile Ile Ser His Thr

-continued

```
                1295                1300                1305

Leu His Arg Ile Leu Gln Pro Thr Ala Thr Asn Gln Gln Asn Lys
    1310                1315                1320

Arg Asn Gln Cys Ser Cys Asn Val Thr Glu Phe Glu Leu Ser Gly
    1325                1330                1335

Ala Met Ala Ile Asp Thr Ser Asn Leu Glu Lys Pro Leu Ile Tyr
    1340                1345                1350

Phe Ala Lys Ala Gln Glu Ile Trp Ala Met Asp Leu Glu Gly Cys
    1355                1360                1365

Gln Cys Trp Arg Val Ile Thr Val Pro Ala Met Leu Ala Gly Lys
    1370                1375                1380

Thr Leu Val Ser Leu Thr Val Asp Gly Asp Leu Ile Tyr Trp Ile
    1385                1390                1395

Ile Thr Ala Lys Asp Ser Thr Gln Ile Tyr Gln Ala Lys Lys Gly
    1400                1405                1410

Asn Gly Ala Ile Val Ser Gln Val Lys Ala Leu Arg Ser Arg His
    1415                1420                1425

Ile Leu Ala Tyr Ser Ser Val Met Gln Pro Phe Pro Asp Lys Ala
    1430                1435                1440

Phe Leu Ser Leu Ala Ser Asp Thr Val Glu Pro Thr Ile Leu Asn
    1445                1450                1455

Ala Thr Asn Thr Ser Leu Thr Ile Arg Leu Pro Leu Ala Lys Thr
    1460                1465                1470

Asn Leu Thr Trp Tyr Gly Ile Thr Ser Pro Thr Pro Thr Tyr Leu
    1475                1480                1485

Val Tyr Tyr Ala Glu Val Asn Asp Arg Lys Asn Ser Ser Asp Leu
    1490                1495                1500

Lys Tyr Arg Ile Leu Glu Phe Gln Asp Ser Ile Ala Leu Ile Glu
    1505                1510                1515

Asp Leu Gln Pro Phe Ser Thr Tyr Met Ile Gln Ile Ala Val Lys
    1520                1525                1530

Asn Tyr Tyr Ser Asp Pro Leu Glu His Leu Pro Pro Gly Lys Glu
    1535                1540                1545

Ile Trp Gly Lys Thr Lys Asn Gly Val Pro Glu Ala Val Gln Leu
    1550                1555                1560

Ile Asn Thr Thr Val Arg Ser Asp Thr Ser Leu Ile Ile Ser Trp
    1565                1570                1575

Arg Glu Ser His Lys Pro Asn Gly Pro Lys Glu Ser Val Arg Tyr
    1580                1585                1590

Gln Leu Ala Ile Ser His Leu Ala Leu Ile Pro Glu Thr Pro Leu
    1595                1600                1605

Arg Gln Ser Glu Phe Pro Asn Gly Arg Leu Thr Leu Leu Val Thr
    1610                1615                1620

Arg Leu Ser Gly Gly Asn Ile Tyr Val Leu Lys Val Leu Ala Cys
    1625                1630                1635

His Ser Glu Glu Met Trp Cys Thr Glu Ser His Pro Val Thr Val
    1640                1645                1650

Glu Met Phe Asn Thr Pro Glu Lys Pro Tyr Ser Leu Val Pro Glu
    1655                1660                1665

Asn Thr Ser Leu Gln Phe Asn Trp Lys Ala Pro Leu Asn Val Asn
    1670                1675                1680

Leu Ile Arg Phe Trp Val Glu Leu Gln Lys Trp Lys Tyr Asn Glu
    1685                1690                1695
```

-continued

Phe Tyr His Val Lys Thr Ser Cys Ser Gln Gly Pro Ala Tyr Val
    1700                1705                1710

Cys Asn Ile Thr Asn Leu Gln Pro Tyr Thr Ser Tyr Asn Val Arg
    1715                1720                1725

Val Val Val Val Tyr Lys Thr Gly Glu Asn Ser Thr Ser Leu Pro
    1730                1735                1740

Glu Ser Phe Lys Thr Lys Ala Gly Val Pro Asn Lys Pro Gly Ile
    1745                1750                1755

Pro Lys Leu Leu Glu Gly Ser Lys Asn Ser Ile Gln Trp Glu Lys
    1760                1765                1770

Ala Glu Asp Asn Gly Cys Arg Ile Thr Tyr Tyr Ile Leu Glu Ile
    1775                1780                1785

Arg Lys Ser Thr Ser Asn Asn Leu Gln Asn Gln Asn Leu Arg Trp
    1790                1795                1800

Lys Met Thr Phe Asn Gly Ser Cys Ser Ser Val Cys Thr Trp Lys
    1805                1810                1815

Ser Lys Asn Leu Lys Gly Ile Phe Gln Phe Arg Val Val Ala Ala
    1820                1825                1830

Asn Asn Leu Gly Phe Gly Glu Tyr Ser Gly Ile Ser Glu Asn Ile
    1835                1840                1845

Ile Leu Val Gly Asp Asp Phe Trp Ile Pro Glu Thr Ser Phe Ile
    1850                1855                1860

Leu Thr Ile Ile Val Gly Ile Phe Leu Val Val Thr Ile Pro Leu
    1865                1870                1875

Thr Phe Val Trp His Arg Arg Leu Lys Asn Gln Lys Ser Ala Lys
    1880                1885                1890

Glu Gly Val Thr Val Leu Ile Asn Glu Asp Lys Glu Leu Ala Glu
    1895                1900                1905

Leu Arg Gly Leu Ala Ala Gly Val Gly Leu Ala Asn Ala Cys Tyr
    1910                1915                1920

Ala Ile His Thr Leu Pro Thr Gln Glu Glu Ile Glu Asn Leu Pro
    1925                1930                1935

Ala Phe Pro Arg Glu Lys Leu Thr Leu Arg Leu Leu Leu Gly Ser
    1940                1945                1950

Gly Ala Phe Gly Glu Val Tyr Glu Gly Thr Ala Val Asp Ile Leu
    1955                1960                1965

Gly Val Gly Ser Gly Glu Ile Lys Val Ala Val Lys Thr Leu Lys
    1970                1975                1980

Lys Gly Ser Thr Asp Gln Glu Lys Ile Glu Phe Leu Lys Glu Ala
    1985                1990                1995

His Leu Met Ser Lys Phe Asn His Pro Asn Ile Leu Lys Gln Leu
    2000                2005                2010

Gly Val Cys Leu Leu Asn Glu Pro Gln Tyr Ile Ile Leu Glu Leu
    2015                2020                2025

Met Glu Gly Gly Asp Leu Leu Thr Tyr Leu Arg Lys Ala Arg Met
    2030                2035                2040

Ala Thr Phe Tyr Gly Pro Leu Leu Thr Leu Val Asp Leu Val Asp
    2045                2050                2055

Leu Cys Val Asp Ile Ser Lys Gly Cys Val Tyr Leu Glu Arg Met
    2060                2065                2070

His Phe Ile His Arg Asp Leu Ala Ala Arg Asn Cys Leu Val Ser
    2075                2080                2085

```
Val Lys Asp Tyr Thr Ser Pro Arg Ile Val Lys Ile Gly Asp Phe
    2090                2095                2100

Gly Leu Ala Arg Asp Ile Tyr Lys Asn Asp Tyr Tyr Arg Lys Arg
    2105                2110                2115

Gly Glu Gly Leu Leu Pro Val Arg Trp Met Ala Pro Glu Ser Leu
    2120                2125                2130

Met Asp Gly Ile Phe Thr Thr Gln Ser Asp Val Trp Ser Phe Gly
    2135                2140                2145

Ile Leu Ile Trp Glu Ile Leu Thr Leu Gly His Gln Pro Tyr Pro
    2150                2155                2160

Ala His Ser Asn Leu Asp Val Leu Asn Tyr Val Gln Thr Gly Gly
    2165                2170                2175

Arg Leu Glu Pro Pro Arg Asn Cys Pro Asp Asp Leu Trp Asn Leu
    2180                2185                2190

Met Thr Gln Cys Trp Ala Gln Glu Pro Asp Gln Arg Pro Thr Phe
    2195                2200                2205

His Arg Ile Gln Asp Gln Leu Gln Leu Phe Arg Asn Phe Phe Leu
    2210                2215                2220

Asn Ser Ile Tyr Lys Ser Arg Asp Glu Ala Asn Asn Ser Gly Val
    2225                2230                2235

Ile Asn Glu Ser Phe Glu Gly Glu Asp Gly Asp Val Ile Cys Leu
    2240                2245                2250

Asn Ser Asp Asp Ile Met Pro Val Ala Leu Met Glu Thr Lys Asn
    2255                2260                2265

Arg Glu Gly Leu Asn Tyr Met Val Leu Ala Thr Glu Cys Gly Gln
    2270                2275                2280

Gly Glu Glu Lys Ser Glu Gly Pro Leu Gly Ser Gln Glu Ser Glu
    2285                2290                2295

Ser Cys Gly Leu Arg Lys Glu Glu Lys Glu Pro His Ala Asp Lys
    2300                2305                2310

Asp Phe Cys Gln Glu Lys Gln Val Ala Tyr Cys Pro Ser Gly Lys
    2315                2320                2325

Pro Glu Gly Leu Asn Tyr Ala Cys Leu Thr His Ser Gly Tyr Gly
    2330                2335                2340

Asp Gly Ser Asp
    2345

<210> SEQ ID NO 2
<211> LENGTH: 2227
<212> TYPE: PRT
<213> ORGANISM: Homo sapiens

<400> SEQUENCE: 2

Ser Ala Asn Phe Ser Gly Val Lys Tyr Ile Ile Gln Trp Lys Tyr Ala
1               5                   10                  15

Gln Leu Leu Gly Ser Trp Thr Tyr Thr Lys Thr Val Ser Arg Pro Ser
                20                  25                  30

Tyr Val Val Lys Pro Leu His Pro Phe Thr Glu Tyr Ile Phe Arg Val
            35                  40                  45

Val Trp Ile Phe Thr Ala Gln Leu Gln Leu Tyr Ser Pro Pro Ser Pro
        50                  55                  60

Ser Tyr Arg Thr His Pro His Gly Val Pro Glu Thr Ala Pro Leu Ile
65                  70                  75                  80

Arg Asn Ile Glu Ser Ser Ser Pro Asp Thr Val Glu Val Ser Trp Asp
                85                  90                  95
```

-continued

Pro Pro Gln Phe Pro Gly Gly Pro Ile Leu Gly Tyr Asn Leu Arg Leu
            100                 105                 110

Ile Ser Lys Asn Gln Lys Leu Asp Ala Gly Thr Gln Arg Thr Ser Phe
        115                 120                 125

Gln Phe Tyr Ser Thr Leu Pro Asn Thr Ile Tyr Arg Phe Ser Ile Ala
    130                 135                 140

Ala Val Asn Glu Val Gly Glu Gly Pro Glu Ala Glu Ser Ser Ile Thr
145                 150                 155                 160

Thr Ser Ser Ser Ala Val Gln Gln Glu Glu Gln Trp Leu Phe Leu Ser
                165                 170                 175

Arg Lys Thr Ser Leu Arg Lys Arg Ser Leu Lys His Leu Val Asp Glu
            180                 185                 190

Ala His Cys Leu Arg Leu Asp Ala Ile Tyr His Asn Ile Thr Gly Ile
        195                 200                 205

Ser Val Asp Val His Gln Gln Ile Val Tyr Phe Ser Glu Gly Thr Leu
    210                 215                 220

Ile Trp Ala Lys Lys Ala Ala Asn Met Ser Asp Val Ser Asp Leu Arg
225                 230                 235                 240

Ile Phe Tyr Arg Gly Ser Gly Leu Ile Ser Ser Ile Ser Ile Asp Trp
                245                 250                 255

Leu Tyr Gln Arg Met Tyr Phe Ile Met Asp Glu Leu Val Cys Val Cys
            260                 265                 270

Asp Leu Glu Asn Cys Ser Asn Ile Glu Glu Ile Thr Pro Pro Ser Ile
        275                 280                 285

Ser Ala Pro Gln Lys Ile Val Ala Asp Ser Tyr Asn Gly Tyr Val Phe
    290                 295                 300

Tyr Leu Leu Arg Asp Gly Ile Tyr Arg Ala Asp Leu Pro Val Pro Ser
305                 310                 315                 320

Gly Arg Cys Ala Glu Ala Val Arg Ile Val Glu Ser Cys Thr Leu Lys
                325                 330                 335

Asp Phe Ala Ile Lys Pro Gln Ala Lys Arg Ile Ile Tyr Phe Asn Asp
            340                 345                 350

Thr Ala Gln Val Phe Met Ser Thr Phe Leu Asp Gly Ser Ala Ser His
        355                 360                 365

Leu Ile Leu Pro Arg Ile Pro Phe Ala Asp Val Lys Ser Phe Ala Cys
    370                 375                 380

Glu Asn Asn Asp Phe Leu Val Thr Asp Gly Lys Val Ile Phe Gln Gln
385                 390                 395                 400

Asp Ala Leu Ser Phe Asn Glu Phe Ile Val Gly Cys Asp Leu Ser His
                405                 410                 415

Ile Glu Glu Phe Gly Phe Gly Asn Leu Val Ile Phe Gly Ser Ser Ser
            420                 425                 430

Gln Leu His Pro Leu Pro Gly Arg Pro Gln Glu Leu Ser Val Leu Phe
        435                 440                 445

Gly Ser His Gln Ala Leu Val Gln Trp Lys Pro Pro Ala Leu Ala Ile
    450                 455                 460

Gly Ala Asn Val Ile Leu Ile Ser Asp Ile Ile Glu Leu Phe Glu Leu
465                 470                 475                 480

Gly Pro Ser Ala Trp Gln Asn Trp Thr Tyr Glu Val Lys Val Ser Thr
                485                 490                 495

Gln Asp Pro Pro Glu Val Thr His Ile Phe Leu Asn Ile Ser Gly Thr
            500                 505                 510

```
Met Leu Asn Val Pro Glu Leu Gln Ser Ala Met Lys Tyr Lys Val Ser
            515                 520                 525

Val Arg Ala Ser Ser Pro Lys Arg Pro Gly Pro Trp Ser Glu Pro Ser
530                 535                 540

Val Gly Thr Thr Leu Val Pro Ala Ser Glu Pro Pro Phe Ile Met Ala
545                 550                 555                 560

Val Lys Glu Asp Gly Leu Trp Ser Lys Pro Leu Asn Ser Phe Gly Pro
                565                 570                 575

Gly Glu Phe Leu Ser Ser Asp Ile Gly Asn Val Ser Asp Met Asp Trp
                580                 585                 590

Tyr Asn Asn Ser Leu Tyr Tyr Ser Asp Thr Lys Gly Asp Val Phe Val
            595                 600                 605

Trp Leu Leu Asn Gly Thr Asp Ile Ser Glu Asn Tyr His Leu Pro Ser
610                 615                 620

Ile Ala Gly Ala Gly Ala Leu Ala Phe Glu Trp Leu Gly His Phe Leu
625                 630                 635                 640

Tyr Trp Ala Gly Lys Thr Tyr Val Ile Gln Arg Gln Ser Val Leu Thr
                645                 650                 655

Gly His Thr Asp Ile Val Thr His Val Lys Leu Leu Val Asn Asp Met
                660                 665                 670

Val Val Asp Ser Val Gly Gly Tyr Leu Tyr Trp Thr Thr Leu Tyr Ser
            675                 680                 685

Val Glu Ser Thr Arg Leu Asn Gly Glu Ser Ser Leu Val Leu Gln Thr
            690                 695                 700

Gln Pro Trp Phe Ser Gly Lys Lys Val Ile Ala Leu Thr Leu Asp Leu
705                 710                 715                 720

Ser Asp Gly Leu Leu Tyr Trp Leu Val Gln Asp Ser Gln Cys Ile His
                725                 730                 735

Leu Tyr Thr Ala Val Leu Arg Gly Gln Ser Thr Gly Asp Thr Thr Ile
                740                 745                 750

Thr Glu Phe Ala Ala Trp Ser Thr Ser Glu Ile Ser Gln Asn Ala Leu
            755                 760                 765

Met Tyr Tyr Ser Gly Arg Leu Phe Trp Ile Asn Gly Phe Arg Ile Ile
            770                 775                 780

Thr Thr Gln Glu Ile Gly Gln Lys Thr Ser Val Ser Val Leu Glu Pro
785                 790                 795                 800

Ala Arg Phe Asn Gln Phe Thr Ile Ile Gln Thr Ser Leu Lys Pro Leu
                805                 810                 815

Pro Gly Asn Phe Ser Phe Thr Pro Lys Val Ile Pro Asp Ser Val Gln
                820                 825                 830

Glu Ser Ser Phe Arg Ile Glu Gly Asn Ala Ser Ser Phe Gln Ile Leu
            835                 840                 845

Trp Asn Gly Pro Pro Ala Val Asp Trp Gly Val Val Phe Tyr Ser Val
850                 855                 860

Glu Phe Ser Ala His Ser Lys Phe Leu Ala Ser Glu Gln His Ser Leu
865                 870                 875                 880

Pro Val Phe Thr Val Glu Gly Leu Glu Pro Tyr Ala Leu Phe Asn Leu
                885                 890                 895

Ser Val Thr Pro Tyr Thr Tyr Trp Gly Lys Gly Pro Lys Thr Ser Leu
                900                 905                 910

Ser Leu Arg Ala Pro Glu Thr Val Pro Ser Ala Pro Glu Asn Pro Arg
            915                 920                 925

Ile Phe Ile Leu Pro Ser Gly Lys Cys Cys Asn Lys Asn Glu Val Val
```

-continued

```
                930             935             940
Val Glu Phe Arg Trp Asn Lys Pro Lys His Glu Asn Gly Val Leu Thr
945                 950             955                 960

Lys Phe Glu Ile Phe Tyr Asn Ile Ser Asn Gln Ser Ile Thr Asn Lys
                965             970             975

Thr Cys Glu Asp Trp Ile Ala Val Asn Val Thr Pro Ser Val Met Ser
            980             985             990

Phe Gln Leu Glu Gly Met Ser Pro Arg Cys Phe Ile Ala Phe Gln Val
        995             1000            1005

Arg Ala Phe Thr Ser Lys Gly Pro Gly Pro Tyr Ala Asp Val Val
    1010            1015            1020

Lys Ser Thr Thr Ser Glu Ile Asn Pro Phe Pro His Leu Ile Thr
    1025            1030            1035

Leu Leu Gly Asn Lys Ile Val Phe Leu Asp Met Asp Gln Asn Gln
    1040            1045            1050

Val Val Trp Thr Phe Ser Ala Glu Arg Val Ile Ser Ala Val Cys
    1055            1060            1065

Tyr Thr Ala Asp Asn Glu Met Gly Tyr Tyr Ala Glu Gly Asp Ser
    1070            1075            1080

Leu Phe Leu Leu His Leu His Asn Arg Ser Ser Ser Glu Leu Phe
    1085            1090            1095

Gln Asp Ser Leu Val Phe Asp Ile Thr Val Ile Thr Ile Asp Trp
    1100            1105            1110

Ile Ser Arg His Leu Tyr Phe Ala Leu Lys Glu Ser Gln Asn Gly
    1115            1120            1125

Met Gln Val Phe Asp Val Asp Leu Glu His Lys Val Lys Tyr Pro
    1130            1135            1140

Arg Glu Val Lys Ile His Asn Arg Asn Ser Thr Ile Ile Ser Phe
    1145            1150            1155

Ser Val Tyr Pro Leu Leu Ser Arg Leu Tyr Trp Thr Glu Val Ser
    1160            1165            1170

Asn Phe Gly Tyr Gln Met Phe Tyr Tyr Ser Ile Ile Ser His Thr
    1175            1180            1185

Leu His Arg Ile Leu Gln Pro Thr Ala Thr Asn Gln Gln Asn Lys
    1190            1195            1200

Arg Asn Gln Cys Ser Cys Asn Val Thr Glu Phe Glu Leu Ser Gly
    1205            1210            1215

Ala Met Ala Ile Asp Thr Ser Asn Leu Glu Lys Pro Leu Ile Tyr
    1220            1225            1230

Phe Ala Lys Ala Gln Glu Ile Trp Ala Met Asp Leu Glu Gly Cys
    1235            1240            1245

Gln Cys Trp Arg Val Ile Thr Val Pro Ala Met Leu Ala Gly Lys
    1250            1255            1260

Thr Leu Val Ser Leu Thr Val Asp Gly Asp Leu Ile Tyr Trp Ile
    1265            1270            1275

Ile Thr Ala Lys Asp Ser Thr Gln Ile Tyr Gln Ala Lys Lys Gly
    1280            1285            1290

Asn Gly Ala Ile Val Ser Gln Val Lys Ala Leu Arg Ser Arg His
    1295            1300            1305

Ile Leu Ala Tyr Ser Ser Val Met Gln Pro Phe Pro Asp Lys Ala
    1310            1315            1320

Phe Leu Ser Leu Ala Ser Asp Thr Val Glu Pro Thr Ile Leu Asn
    1325            1330            1335
```

-continued

Ala Thr Asn Thr Ser Leu Thr Ile Arg Leu Pro Leu Ala Lys Thr
1340                    1345                1350

Asn Leu Thr Trp Tyr Gly Ile Thr Ser Pro Thr Pro Thr Tyr Leu
1355                    1360                1365

Val Tyr Tyr Ala Glu Val Asn Asp Arg Lys Asn Ser Ser Asp Leu
1370                    1375                1380

Lys Tyr Arg Ile Leu Glu Phe Gln Asp Ser Ile Ala Leu Ile Glu
1385                    1390                1395

Asp Leu Gln Pro Phe Ser Thr Tyr Met Ile Gln Ile Ala Val Lys
1400                    1405                1410

Asn Tyr Tyr Ser Asp Pro Leu Glu His Leu Pro Pro Gly Lys Glu
1415                    1420                1425

Ile Trp Gly Lys Thr Lys Asn Gly Val Pro Glu Ala Val Gln Leu
1430                    1435                1440

Ile Asn Thr Thr Val Arg Ser Asp Thr Ser Leu Ile Ile Ser Trp
1445                    1450                1455

Arg Glu Ser His Lys Pro Asn Gly Pro Lys Glu Ser Val Arg Tyr
1460                    1465                1470

Gln Leu Ala Ile Ser His Leu Ala Leu Ile Pro Glu Thr Pro Leu
1475                    1480                1485

Arg Gln Ser Glu Phe Pro Asn Gly Arg Leu Thr Leu Leu Val Thr
1490                    1495                1500

Arg Leu Ser Gly Gly Asn Ile Tyr Val Leu Lys Val Leu Ala Cys
1505                    1510                1515

His Ser Glu Glu Met Trp Cys Thr Glu Ser His Pro Val Thr Val
1520                    1525                1530

Glu Met Phe Asn Thr Pro Glu Lys Pro Tyr Ser Leu Val Pro Glu
1535                    1540                1545

Asn Thr Ser Leu Gln Phe Asn Trp Lys Ala Pro Leu Asn Val Asn
1550                    1555                1560

Leu Ile Arg Phe Trp Val Glu Leu Gln Lys Trp Lys Tyr Asn Glu
1565                    1570                1575

Phe Tyr His Val Lys Thr Ser Cys Ser Gln Gly Pro Ala Tyr Val
1580                    1585                1590

Cys Asn Ile Thr Asn Leu Gln Pro Tyr Thr Ser Tyr Asn Val Arg
1595                    1600                1605

Val Val Val Val Tyr Lys Thr Gly Glu Asn Ser Thr Ser Leu Pro
1610                    1615                1620

Glu Ser Phe Lys Thr Lys Ala Gly Val Pro Asn Lys Pro Gly Ile
1625                    1630                1635

Pro Lys Leu Leu Glu Gly Ser Lys Asn Ser Ile Gln Trp Glu Lys
1640                    1645                1650

Ala Glu Asp Asn Gly Cys Arg Ile Thr Tyr Tyr Ile Leu Glu Ile
1655                    1660                1665

Arg Lys Ser Thr Ser Asn Asn Leu Gln Asn Gln Asn Leu Arg Trp
1670                    1675                1680

Lys Met Thr Phe Asn Gly Ser Cys Ser Ser Val Cys Thr Trp Lys
1685                    1690                1695

Ser Lys Asn Leu Lys Gly Ile Phe Gln Phe Arg Val Val Ala Ala
1700                    1705                1710

Asn Asn Leu Gly Phe Gly Glu Tyr Ser Gly Ile Ser Glu Asn Ile
1715                    1720                1725

```
Ile Leu Val Gly Asp Asp Phe Trp Ile Pro Glu Thr Ser Phe Ile
1730                1735                1740

Leu Thr Ile Ile Val Gly Ile Phe Leu Val Val Thr Ile Pro Leu
1745                1750                1755

Thr Phe Val Trp His Arg Arg Leu Lys Asn Gln Lys Ser Ala Lys
1760                1765                1770

Glu Gly Val Thr Val Leu Ile Asn Glu Asp Lys Glu Leu Ala Glu
1775                1780                1785

Leu Arg Gly Leu Ala Ala Gly Val Gly Leu Ala Asn Ala Cys Tyr
1790                1795                1800

Ala Ile His Thr Leu Pro Thr Gln Glu Glu Ile Glu Asn Leu Pro
1805                1810                1815

Ala Phe Pro Arg Glu Lys Leu Thr Leu Arg Leu Leu Leu Gly Ser
1820                1825                1830

Gly Ala Phe Gly Glu Val Tyr Glu Gly Thr Ala Val Asp Ile Leu
1835                1840                1845

Gly Val Gly Ser Gly Glu Ile Lys Val Ala Val Lys Thr Leu Lys
1850                1855                1860

Lys Gly Ser Thr Asp Gln Glu Lys Ile Glu Phe Leu Lys Glu Ala
1865                1870                1875

His Leu Met Ser Lys Phe Asn His Pro Asn Ile Leu Lys Gln Leu
1880                1885                1890

Gly Val Cys Leu Leu Asn Glu Pro Gln Tyr Ile Ile Leu Glu Leu
1895                1900                1905

Met Glu Gly Gly Asn Leu Leu Thr Tyr Leu Arg Lys Ala Arg Met
1910                1915                1920

Ala Thr Phe Tyr Gly Pro Leu Leu Thr Leu Val Asp Leu Val Asp
1925                1930                1935

Leu Cys Val Asp Ile Ser Lys Gly Cys Val Tyr Leu Glu Arg Met
1940                1945                1950

His Phe Ile His Arg Asp Leu Ala Ala Arg Asn Cys Leu Val Ser
1955                1960                1965

Val Lys Asp Tyr Thr Ser Pro Arg Ile Val Lys Ile Gly Asp Phe
1970                1975                1980

Gly Leu Ala Arg Asp Ile Tyr Lys Asn Asp Tyr Tyr Arg Lys Arg
1985                1990                1995

Gly Glu Gly Leu Leu Pro Val Arg Trp Met Ala Pro Glu Ser Leu
2000                2005                2010

Met Asp Gly Ile Phe Thr Thr Gln Ser Asp Val Trp Ser Phe Gly
2015                2020                2025

Ile Leu Ile Trp Glu Ile Leu Thr Leu Gly His Gln Pro Tyr Pro
2030                2035                2040

Ala His Ser Asn Leu Asp Val Leu Asn Tyr Val Gln Thr Gly Gly
2045                2050                2055

Arg Leu Glu Pro Pro Arg Asn Cys Pro Asp Asp Leu Trp Asn Leu
2060                2065                2070

Met Thr Gln Cys Trp Ala Gln Glu Pro Asp Gln Arg Pro Thr Phe
2075                2080                2085

His Arg Ile Gln Asp Gln Leu Gln Leu Phe Arg Asn Phe Phe Leu
2090                2095                2100

Asn Ser Ile Tyr Lys Ser Arg Asp Glu Ala Asn Asn Ser Gly Val
2105                2110                2115

Ile Asn Glu Ser Phe Glu Gly Glu Asp Gly Asp Val Ile Cys Leu
```

```
                       2120                2125                2130
Asn Ser Asp Asp Ile Met Pro Val Ala Leu Met Glu Thr Lys Asn
    2135                2140                2145

Arg Glu Gly Leu Asn Tyr Met Val Leu Ala Thr Glu Cys Gly Gln
    2150                2155                2160

Gly Glu Glu Lys Ser Glu Gly Pro Leu Gly Ser Gln Glu Ser Glu
    2165                2170                2175

Ser Cys Gly Leu Arg Lys Glu Lys Glu Pro His Ala Asp Lys
    2180                2185                2190

Asp Phe Cys Gln Glu Lys Gln Val Ala Tyr Cys Pro Ser Gly Lys
    2195                2200                2205

Pro Glu Gly Leu Asn Tyr Ala Cys Leu Thr His Ser Gly Tyr Gly
    2210                2215                2220

Asp Gly Ser Asp
    2225

<210> SEQ ID NO 3
<211> LENGTH: 7368
<212> TYPE: DNA
<213> ORGANISM: Homo sapiens

<400> SEQUENCE: 3
```

| | | | | | |
|---|---|---|---|---|---|
| caagctttca | agcattcaaa | ggtctaaatg | aaaaaggcta | agtattattt | caaaaggcaa | 60 |
| gtatatccta | atatagcaaa | acaaacaaag | caaaatccat | cagctactcc | tccaattgaa | 120 |
| gtgatgaagc | ccaaataatt | catatagcaa | aatggagaaa | attagaccgg | ccatctaaaa | 180 |
| atctgccatt | ggtgaagtga | tgaagaacat | ttactgtctt | attccgaagc | ttgtcaattt | 240 |
| tgcaactctt | ggctgcctat | ggatttctgt | ggtgcagtgt | acagttttaa | atagctgcct | 300 |
| aaagtcgtgt | gtaactaatc | tgggccagca | gcttgacctt | ggcacaccac | ataatctgag | 360 |
| tgaaccgtgt | atccaaggat | gtcacttttg | gaactctgta | gatcagaaaa | actgtgcttt | 420 |
| aaagtgtcgg | gagtcgtgtg | aggttggctg | tagcagcgcg | gaaggtgcat | atgaagagga | 480 |
| agtactggaa | aatgcagacc | taccaactgc | tcccttgct | tcttccattg | gaagccacaa | 540 |
| tatgacatta | cgatggaaat | ctgcaaactt | ctctggagta | aaatacatca | ttcagtggaa | 600 |
| atatgcacaa | cttctgggaa | gctggactta | tactaagact | gtgtccagac | cgtcctatgt | 660 |
| ggtcaagccc | ctgcaccct | tcactgagta | cattttccga | gtggtttgga | tcttcacagc | 720 |
| gcagctgcag | ctctactccc | tccaagtcc | cagttacagg | actcatcctc | atggagttcc | 780 |
| tgaaactgca | ccttttgatta | ggaatattga | gagctcaagt | cccgacactg | tggaagtcag | 840 |
| ctgggatcca | cctcaattcc | caggtggacc | tattttgggt | tataacttaa | ggctgatcag | 900 |
| caaaaatcaa | aaattagatg | cagggacaca | gagaaccagt | ttccagtttt | actccacttt | 960 |
| accaaatact | atctacaggt | tttctattgc | agcagtaaat | gaagttggtg | agggtccaga | 1020 |
| agcagaatct | agtattacca | cttcatcttc | agcagttcaa | caagaggaac | agtggctctt | 1080 |
| tttatccaga | aaaacttctc | taagaaagag | atctttaaaa | catttagtag | atgaagcaca | 1140 |
| ttgccttcgg | ttggatgcta | taccataa | tattacagga | atatctgttg | atgtccacca | 1200 |
| gcaaattgtt | tatttctctg | aaggaactct | catatgggcg | aagaaggctg | ccaacatgtc | 1260 |
| tgatgtatct | gacctgagaa | tttttacag | aggttcagga | ttaatttctt | ctatctccat | 1320 |
| agattggctt | tatcaaagaa | tgtatttcat | catggatgaa | ctggtatgtg | tctgtgattt | 1380 |
| agagaactgc | tcaaacatcg | aggaaattac | tccacctct | attagtgcac | ctcaaaaaat | 1440 |

-continued

```
tgtggctgat tcatacaatg gtatgtctt ttacctcctg agagatggca tttatagagc    1500
agaccttcct gtaccatctg ccggtgtgc agaagctgtg cgtattgtgg agagttgcac    1560
gttaaaggac tttgcaatca agccacaagc caagcgaatc atttacttca atgacactgc    1620
ccaagtcttc atgtcaacat ttctggatgg ctctgcttcc catctcatcc tacctcgcat    1680
cccctttgct gatgtgaaaa gttttgcttg tgaaaacaat gactttcttg tcacagatgg    1740
caaggtcatt ttccaacagg atgctttgtc ttttaatgaa ttcatcgtgg atgtgacct    1800 gagtcacata gaagaatttg ggtttggtaa cttggtcatc tttggctcat cctcccagct    1860
gcaccctctg ccaggccgcc cgcaggagct tccggtgctg tttggctctc accaggctct    1920
tgttcaatgg aagcctcctg cccttgccat aggagccaat gtcatcctga tcagtgatat    1980
tattgaactc tttgaattag cccttctgc ctggcagaac tggacctatg aggtgaaagt    2040
atccacccaa gaccctcctg aagtcactca tattttcttg aacataagtg gaaccatgct    2100
gaatgtacct gagctgcaga gtgctatgaa atacaaggtt tctgtgagag caagttctcc    2160
aaagaggcca ggcccctggt cagagccctc agtgggtact accctggtgc cagctagtga    2220
accaccattt atcatggctg tgaaagaaga tgggctttgg agtaaaccat taaatagctt    2280
tggcccagga gagttcttat cctctgatat aggaaatgtg tcagacatgg attggtataa    2340
caacagcctc tactacagtg acacgaaagg cgacgttttt gtgtggctgc tgaatgggac    2400
ggatatctca gagaattatc acctacccag cattgcagga gcaggggctt tagcttttga    2460
gtggctgggt cactttctct actgggctgg aaagacatat gtgatacaaa ggcagtctgt    2520
gttgacggga cacacagaca ttgttaccca cgtgaagcta ttggtgaatg acatggtggt    2580
ggattcagtt ggtggatatc tctactggac cacactctat tcagtggaaa gcaccagact    2640
aaatggggaa agttcccttg tactacagac acagccttgg ttttctggga aaaaggtaat    2700
tgctctaact ttagacctca gtgatgggct cctgtattgg ttggttcaag acagtcaatg    2760
tattcacctg tacacagctg ttcttcgggg acagagcact ggggatacca ccatcacaga    2820
atttgcagcc tggagtactt ctgaaatttc ccagaatgca ctgatgtact atagtggtcg    2880
gctgttctgg atcaatggct ttaggattat acaactcaa gaaataggtc agaaaaccag    2940
tgtctctgtt ttggaaccag ccagatttaa tcagttcaca attattcaga catcccttaa    3000 gccctgcca gggaactttt cctttacccc taaggttatt ccagattctg ttcaagagtc    3060
ttcatttagg attgaaggaa atgcttcaag ttttcaaatc ctgtggaatg gtccccctgc    3120
ggtagactgg ggtgtagttt tctacagtgt agaatttagt gctcattcta gttcttggc    3180 tagtgaacaa cactctttac ctgtatttac tgtggaagga ctggaacctt atgccttatt    3240
taatctttct gtcactcctt atacctactg gggaaagggc cccaaaacat ctctgtcact    3300
tcgagcacct gaaacagttc catcagcacc agagaacccc agaatattta tattaccaag    3360
tggaaaatgc tgcaacaaga atgaagttgt ggtggaattt aggtggaaca aacctaagca    3420
tgaaaatggg gtgttaacaa aatttgaaat ttctacaat atatccaatc aaagtattac    3480
aaacaaaaca tgtgaagact ggattgctgt caatgtcact ccctcagtga tgtcttttca    3540
acttgaaggc atgagtccca gatgctttat tgccttccag gttagggcct ttacatctaa    3600
ggggccagga ccatatgctg acgttgtaaa gtctacaaca tcagaaatca acccatttcc    3660
tcacctcata actcttcttg gtaacaagat agtttttta gatatggatc aaaatcaagt    3720
tgtgtggacg ttttcagcag aaagagttat cagtgccgtt tgctacacag ctgataatga    3780
gatgggatat tatgctgaag gggactcact cttttcttctg cacttgcaca atcgctctag    3840
```

-continued

```
ctctgagctt ttccaagatt cactggtttt tgatatcaca gttattacaa ttgactggat    3900
ttcaaggcac ctctactttg cactgaaaga atcacaaaat ggaatgcaag tatttgatgt    3960
tgatcttgaa cacaaggtga aatatcccag agaggtgaag attcacaata ggaattcaac    4020
aataatttct ttttctgtat atcctctttt aagtcgcttg tattggacag aagtttccaa    4080
ttttggctac cagatgttct actacagtat tatcagtcac accttgcacc gaattctgca    4140
acccacagct acaaaccaac aaaacaaaag gaatcaatgt tcttgtaatg tgactgaatt    4200
tgagttaagt ggagcaatgg ctattgatac ctctaaccta gagaaaccat tgatatactt    4260
tgccaaagca caagagatct gggcaatgga tctggaaggc tgtcagtgtt ggagagttat    4320
cacagtacct gctatgctcg caggaaaaac ccttgttagc ttaactgtgg atggagatct    4380
tatatactgg atcatcacag caaaggacag cacacagatt tatcaggcaa agaaaggaaa    4440
tggggccatc gtttcccagg tgaaggccct aaggagtagg catatcttgg cttacagttc    4500
agttatgcag ccttttccag ataaagcgtt tctgtctcta gcttcagaca ctgtggaacc    4560
aactatactt aatgccacta acactagcct cacaatcaga ttacctctgg ccaagacaaa    4620
cctcacatgg tatggcatca ccagccctac tccaacatac ctggtttatt atgcagaagt    4680
taatgacagg aaaaacagct ctgacttgaa atatagaatt ctggaatttc aggacagtat    4740
agctcttatt gaagatttac aaccattttc aacatacatg atacagatag ctgtaaaaaa    4800
ttattattca gatcctttgg aacatttacc accaggaaaa gagatttggg gaaaaactaa    4860
aaatggagta ccagaggcag tgcagctcat taatacaact gtgcggtcag acaccagcct    4920
cattatatct tggagagaat ctcacaagcc aaatggacct aaagaatcag tccgttatca    4980
gttggcaatc tcacacctgg ccctaattcc tgaaactcct ctaagacaaa gtgaatttcc    5040
aaatggaagg ctcactctcc ttgttactag actgtctggt ggaaatattt atgtgttaaa    5100
ggttcttgcc tgccactctg aggaaatgtg gtgtacagag agtcatcctg tcactgtgga    5160
aatgtttaac acaccagaga aaccttattc cttggttcca gagaacacta gtttgcaatt    5220
taattggaag gctccattga atgttaacct catcagattt tgggttgagc tacagaagtg    5280
gaaatacaat gagttttacc atgttaaaac ttcatgcagc caaggtcctg cttatgtctg    5340
taatatcaca aatctacaac cttatacttc atataatgtc agagtagtgg tggtttataa    5400
gacgggagaa aatagcacct cacttccaga aagctttaag acaaaagctg gagtcccaaa    5460
taaaccaggc attcccaaat tactagaagg gagtaaaaat tcaatacagt gggagaaagc    5520
tgaagataat ggatgtagaa ttacatacta tatccttgag ataagaagaa gcacttcaaa    5580
taatttacag aaccagaatt taaggtggaa gatgacattt aatggatcct gcagtagtgt    5640
ttgcacatgg aagtccaaaa acctgaaagg aatatttcag ttcagagtag tagctgcaaa    5700
taatctaggg tttggtgaat atagtggaat cagtgagaat attatattag ttggagatga    5760
tttttggata ccagaaacaa gtttcatact tactattata gttggaatat ttctggttgt    5820
tacaatccca ctgaccttg tctggcatag aagattaaag aatcaaaaaa gtgccaagga    5880 agggtgaca gtgcttataa acgaagacaa agagttggct gagctgcgag tctggcagc    5940 cggagtaggc ctggctaatg cctgctatgc aatacatact cttccaaccc aagaggagat    6000
tgaaaatctt cctgccttcc ctcgggaaaa actgactctg cgtctcttgc tgggaagtgg    6060
agcctttgga gaagtgtatg aaggaacagc agtggacatc ttaggagttg aagtggaga    6120 aatcaaagta gcagtgaaga cttttgaagaa gggttccaca gaccaggaga agattgaatt    6180
```

```
cctgaaggag gcacatctga tgagcaaatt taatcatccc aacattctga agcagcttgg    6240
agtttgtctg ctgaatgaac cccaatacat tatcctggaa ctgatggagg gaggagacct    6300
tcttacttat ttgcgtaaag cccggatggc aacgttttat ggtcctttac tcaccttggt    6360
tgaccttgta gacctgtgtg tagatatttc aaaaggctgt gtctacttgg aacggatgca    6420
tttcattcac agggatctgg cagctagaaa ttgccttgtt tccgtgaaag actataccag    6480
tccacggata gtgaagattg gagactttgg actcgccaga gacatctata aaaatgatta    6540
ctatagaaag agaggggaag gcctgctccc agttcggtgg atggctccag aaagtttgat    6600
ggatggaatc ttcactactc aatctgatgt atggtctttt ggaattctga tttgggagat    6660
tttaactctt ggtcatcagc cttatccagc tcattccaac cttgatgtgt taaactatgt    6720
gcaaacagga gggagactgg agccaccaag aaattgtcct gatgatctgt ggaatttaat    6780
gacccagtgc tgggctcaag aacccgacca aagacctact tttcatagaa ttcaggacca    6840
acttcagtta ttcagaaatt ttttcttaaa tagcatttat aagtccagag atgaagcaaa    6900
caacagtgga gtcataaatg aaagctttga aggtgaagat ggcgatgtga tttgtttgaa    6960
ttcagatgac attatgccag ttgctttaat ggaaacgaag aaccgagaag ggttaaacta    7020
tatggtactt gctacagaat gtggccaagg tgaagaaaag tctgagggtc ctctaggctc    7080
ccaggaatct gaatcttgtg gtctgaggaa agaagagaag gaaccacatg cagacaaaga    7140
tttctgccaa gaaaaacaag tggcttactg cccttctggc aagcctgaag gcctgaacta    7200
tgcctgtctc actcacagtg gatatggaga tgggtctgat taatagcgtt gtttgggaaa    7260
tagagagttg agataaacac tctcattcag tagttactga aagaaaactc tgctagaatg    7320
ataaatgtca tggtggtcta taactccaaa taaacaatgc aacgttcc                 7368
```

METHODS OF DETECTING CANCERS SENSITIVE TO CABOZANTINIB

ACKNOWLEDGEMENT OF GOVERNMENT SUPPORT

The work resulting in this invention was supported by the United States government under the terms of grant number P01CA12943, awarded by the National Institutes of Health. The United States government has certain rights to this invention.

FIELD

Generally the field is molecular diagnostic tests. More specifically, the field is molecular diagnostic tests that detect drug sensitivity in cancer.

BACKGROUND

Chromosomal rearrangements of the receptor tyrosine kinase ROS1 are oncogenic drivers in multiple malignancies (Davare M A and Tognon C E, Biol Cell 107, 111-129 (2015); incorporated by reference herein). Fusion of the intact ROS1 tyrosine kinase domain with various gene partners results in constitutive activation of downstream pathways responsible for tumor growth and proliferation. In lung adenocarcinomas, ROS1 rearrangements comprise a distinct molecular subset of tumors present in 1-2% of patients. CD74-ROS1 is the most common fusion in this context (Rimkunas V M et al, Clin Cancer res 18, 4449-4457 (2012); Takeuchi K et al, Nat Med 18, 378-381 (2012); and Bergethon K et al, J Clin Oncol 30, 863-870 (2012); all of which are incorporated by reference herein).

ROS1-rearranged lung cancers are highly sensitive to treatment with the ROS1/ALK tyrosine kinase inhibitor (TKI) crizotinib (Mazieres J et al, J Clin Oncol 33, 992-999 (2015); incorporated by reference herein), with a response rate of 72% and a median progression-free survival of 19 months based on phase 1 expansion cohort data (Shaw A T et al, N Engl J Med 371, 1963-1971 (2014); incorporated by reference herein). Consistent with the experience with crizotinib in the treatment of advanced ALK-rearranged lung cancers, acquired resistance has also begun to emerge in patients harboring ROS1 fusions Awad M M et al, N Engl J Med 368, 2395-2401 (2013); incorporated by reference herein), although the scope of such resistance mechanisms in this setting remain unknown. Second-generation ROS1 inhibitors are in clinical development and may provide viable treatment options for patients with resistance to crizotinib, but clinical response to these agents has not been published to date.

SUMMARY

Rearranged ROS1 is a crizotinib-sensitive oncogenic driver in lung cancer. The development of acquired resistance, however, poses a serious clinical challenge. Consequently, experimental and clinical validation of resistance mechanisms and potential second-line therapies is essential. Disclosed herein is are diagnostic tests involving the use of a ROS1 D2033N mutation originally found in a patient with CD74-ROS1-rearranged lung adenocarcinoma who had acquired resistance to crizotinib. Crizotinib resistance of CD74-ROS1 D2033N was evaluated using cell based assays and structural modelling. In biochemical and cell-based assays, the CD74-ROS1 D2033N mutant demonstrated significantly less sensitivity to crizotinib than controls. Molecular dynamics simulation revealed compromised crizotinib binding due to drastic changes in the electrostatic interaction between the D2033 residue and crizotinib and reorientation of neighboring residues. In contrast, cabozantinib binding was unaffected by the D2033N substitution and inhibitory potency against the mutant was retained. Notably, cabozantinib treatment resulted in a rapid clinical and near complete radiographic response in this patient. These results provide the first example of successful therapeutic intervention with targeted therapy to overcome crizotinib resistance in a ROS1-rearranged cancer.

The emergence of resistance to targeted therapy is a recurrent clinical challenge and requires development and validation of secondary agents with improved activity. Accompanied by experimental cell-based and structural validation, this report of a near complete response to cabozantinib in a ROS1-rearranged lung adenocarcinoma patient with acquired resistance to crizotinib mediated by a novel CD74-ROS1 D2033N solvent-front mutation provides the first clinical example of crizotinib resistance overcome by targeted therapy in a ROS1-rearranged malignancy.

Disclosed herein is the identification of a novel ROS1 solvent-front mutation in a patient with a CD74-ROS1-rearranged lung adenocarcinoma who developed acquired resistance to crizotinib. Treatment with cabozantinib—an FDA-approved TKI with activity against ROS1—resulted in rapid clinical and radiographic responses, providing the first example of overcoming crizotinib resistance with oral targeted therapy in a patient with a ROS1-rearranged malignancy. Furthermore, validation of and structural insight into the mechanism of resistance to crizotinib and the efficacy of cabozantinib are disclosed.

Disclosed are methods of treating a subject with a solid tumor, particularly when the solid tumor is characterized by a ROS1 fusion. In one embodiment, the method involves receiving a sample from the subject that includes a portion of the solid tumor and amplifying a polynucleotide fragment from the sample. The polynucleotide fragment includes bases 6295-6297 of SEQ ID NO: 3 herein. The method further involves detecting a mutation in bases 6295-6297 that results in an amino acid substitution. The method further involves administering a pharmaceutical composition comprising cabozantinib to the subject, thereby treating the subject. The amino acid substitution can correspond to a D2033N amino acid substitution in SEQ ID NO: 1. The cancer can be any cancer with a ROS1 fusion such as a non-small cell lung cancer. The method can further involve sequencing the polynucleotide fragment using Sanger sequencing. The method can further involve isolating tumor genomic DNA or tumor messenger RNA from the sample prior to amplification. The method can further involve obtaining the sample from the subject. The method can further involve detecting the ROS-1 fusion by fluorescent in situ hybridization or by nucleic acid sequencing.

In another embodiment, the method involves receiving a sample from the subject, where the sample includes isolated tumor genomic DNA or tumor messenger RNA. The method further involves amplifying a nucleic acid fragment from SEQ ID NO: 3, where the fragment includes bases 6295-6297 of SEQ ID NO: 3, and administering a pharmaceutical composition comprising cabozantinib to the subject, thereby treating the subject. The amino acid substitution can correspond to a D2033N amino acid substitution. The cancer can be any cancer with a ROS1 fusion such as a non-small cell lung cancer. The method can further involve sequencing the nucleic acid fragment using Sanger sequencing.

BRIEF DESCRIPTION OF THE SEVERAL VIEWS OF THE DRAWINGS

FIG. 9 is a table describing treatment history of a patient treated using the disclosed methods.

SEQUENCE LISTING

Figure 1:
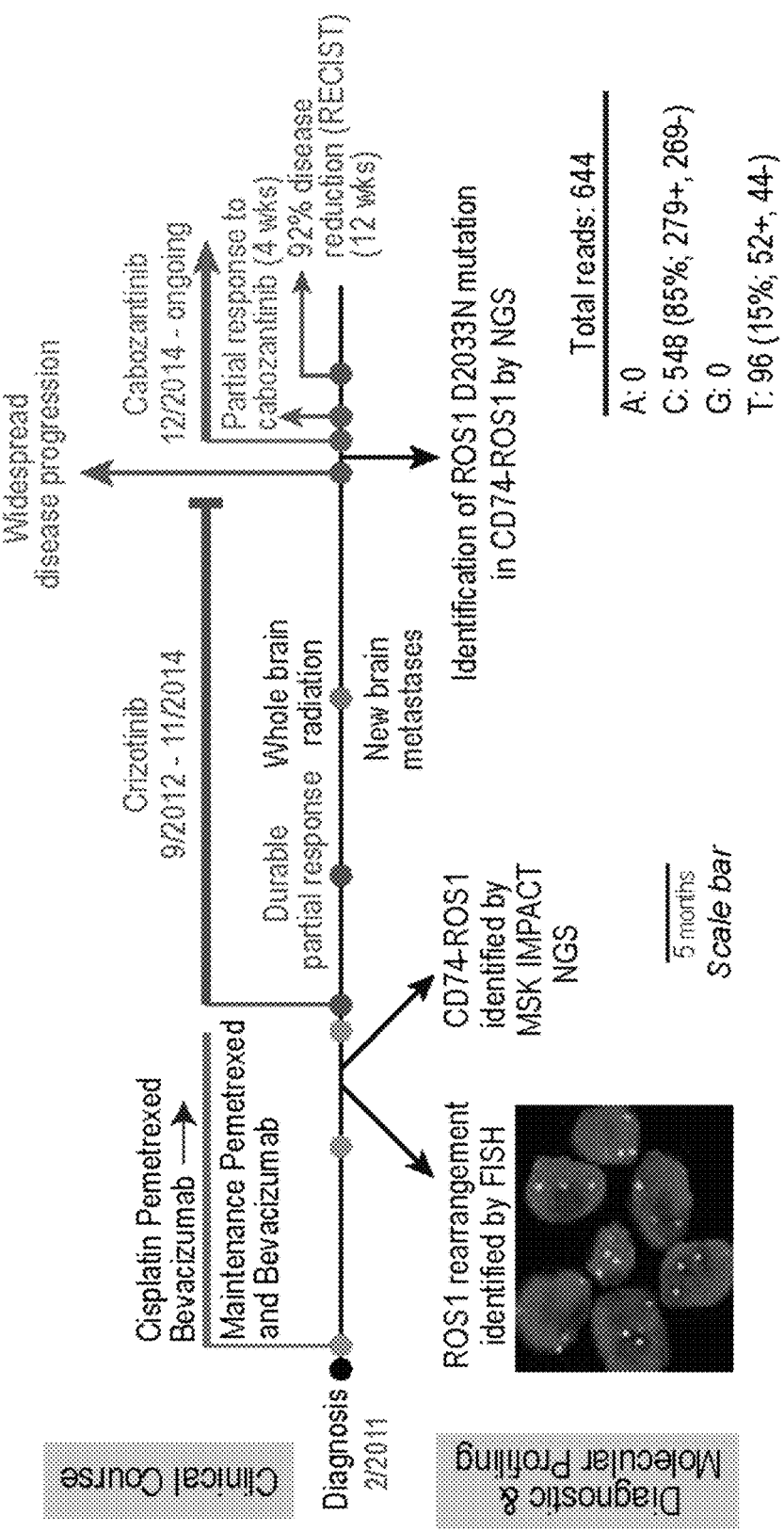
FIG. 1: A patient with CD74-ROS1-rearranged lung adenocarcinoma and acquired resistance to crizotinib mediated by a novel CD74-ROS1D2033N mutation responds to therapy with cabozantinib. The patient's clinical course and treatment history are depicted chronologically moving left to right. Rearranged ROS1 was initially detected via break-apart FISH assay. Split green (5' probe) and red (3' probe) signals indicate the presence of a ROS1 fusion, subsequently identified as CD74-ROS1. Broad, hybrid-capture next-generation sequencing of pre- and post-crizotinib tumor detected an acquired c.6097G>A (D2033N) mutation within the ROS1 kinase domain at the time of disease progression. A partial response to cabozantinib (RECIST v1.1) was achieved and confirmed at 8 weeks. This was accompanied by a clinical response to therapy (substantial improvement in cough and abdominal discomfort) noted within a few days of cabozantinib initiation. At 12 weeks, a near complete response was noted with a 92% reduction in disease burden.

SEQ ID NO: 1 is a protein sequence of a CD74-ROS1 fusion.

SEQ ID NO: 2 is a protein sequence of a CD74-ROS1 fusion with a D2033N mutation.

SEQ ID NO: 3 is a polynucleotide sequence of CD74-ROS1 fusion mRNA.

DETAILED DESCRIPTION

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell 10 Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for polynucleotides or polypeptides are approximate, and are provided for description. Although methods and materials similar or equivalent to those described herein can be used in the practice or testing of this disclosure, suitable methods and materials are described below.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise or consist of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified.

In addition, the materials, methods, and examples are illustrative only and not intended to be limiting. In order to facilitate review of the various embodiments of the disclosure, the following explanations of specific terms are provided:

Aberrant activity of a tyrosine kinase: Inappropriate or uncontrolled activation of a tyrosine kinase, such as ROS1, for example by over-expression, upstream activation (for example, by upstream activation of a protein that affect a tyrosine kinase), and/or mutation (for example a truncation, deletion, insertion and/or translocation which increases the activity, such as but not limited to, kinase activity of a tyrosine kinase), which can lead to uncontrolled cell growth, for example in cancer, including adenocarcinoma. In some examples, aberrant activity of a tyrosine kinase is a higher rate of kinase activity than the unmutated tyrosine kinase. In some examples, aberrant activity of a tyrosine kinase is a lower rate of kinase activity than the unmutated tyrosine kinase. Other examples of aberrant activity of a tyrosine kinase include, but are not limited to, mislocalization of the tyrosine kinase, for example mislocalization in an organelle of a cell or mislocalization at the cell membrane relative to the unmutated tyrosine kinase.

Administration: To provide or give a subject an agent, such as a composition that targets/inhibits a ROS1 kinase (such as cabozantinib) by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Amplifying a nucleic acid molecule: To increase the number of copies of a polynucleotide molecule, such as a gene or fragment of a gene, for example a region of a gene that encodes a tumor biomarker, such a fragment of SEQ ID NO: 3, that includes nucleotides 6295-6297. The resulting products are called amplification products. An example of in vitro amplification is the polymerase chain reaction (PCR). Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see WO90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

A commonly used method for real-time quantitative polymerase chain reaction involves the use of a double stranded DNA dye (such as SYBR Green I dye). For example, as the amount of PCR product increases, more SYBR Green I dye binds to DNA, resulting in a steady increase in fluorescence. SYBR green binds to double stranded DNA, but not to single stranded DNA. In addition, SYBR green fluoresces strongly at a wavelength of 497 nm when it is bound to double stranded DNA, but does not fluoresce when it is not bound to double stranded DNA. As a result, the intensity of fluorescence at 497 nm may be correlated with the amount of amplification product present at any time during the reaction. The rate of amplification may in turn be correlated with the amount of template sequence present in the initial sample. Generally, Ct values are calculated similarly to those calculated using the TaqMan® system. Because the probe is absent, amplification of the proper sequence may be checked by any of a number of techniques. One such technique involves running the amplification products on an agarose or other gel appropriate for resolving polynucleotide fragments and comparing the amplification products from the quantitative real time PCR reaction with control DNA fragments of known size.

Another commonly used method is real-time quantitative TaqMan® PCR (Applied Biosystems). This type of PCR has reduced the variability traditionally associated with quantitative PCR, thus allowing the routine and reliable quantification of PCR products to produce sensitive, accurate, and reproducible measurements of levels of gene expression. The PCR step can use any of a number of thermostable DNA-dependent DNA polymerases, it typically employs a Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used.

Two oligonucleotide primers are used to generate an amplicon typical of a PCR reaction. A third oligonucleotide, or probe, is designed to detect nucleotide sequence located between the two PCR primers. The probe is nonextendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Examples of fluorescent labels that may be used in quantitative PCR include but need not be limited to: HEX, TET, 6-FAM, JOE, Cy3, Cy5, ROX TAMRA, and Texas Red. Examples of quenchers that may be used in quantitative PCR include, but need not be limited to TAMRA (which may be used as a quencher with HEX, TET, or 6-FAM), BHQ1, BHQ2, or DABCYL. TAQMAN® RT-PCR can be performed using commercially available equipment, such as, for example, ABI PRISM 7700® Sequence Detection System (Perkin-Elmer-Applied Biosystems), or LightCycler® (Roche Molecular Biochemicals).

In one embodiment, the 5' nuclease procedure is run on a real-time quantitative PCR device such as the ABI PRISM 7700® Sequence Detection System. The system includes a thermocycler, laser, charge-coupled device (CCD), camera and computer. The system amplifies samples in a 96-well format on a thermocycler. During amplification, laser-induced fluorescent signal is collected in real time through fiber optic cables for all 96 wells, and detected at the CCD. The system includes software for running the instrument and for analyzing the data. In some examples, 5'-nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR can be performed using an internal standard. The ideal internal standard is expressed at a constant level among different tissues, and is unaffected by the experimental treatment. RNAs most frequently used to normalize patterns of gene expression are the mRNA products of housekeeping genes such as GADPH, actin, and others.

Amplification of a polynucleotide sequence may be used for any of a number of purposes, including increasing the amount of a rare sequence to be analyzed by other methods. It may also be used to identify a sequence directly (for example, though an amplification refractory mutation system) or as part of a DNA sequencing method.

Antibody: A polypeptide including at least a light chain or heavy chain immunoglobulin variable region which specifically recognizes and binds an epitope of an antigen or a fragment thereof. Antibodies are composed of a heavy and a light chain, each of which has a variable region, termed the variable heavy (VH) region and the variable light (VL) region. Together, the VH region and the VL region are responsible for binding the antigen recognized by the antibody. The VH and VL regions can be further segmented into complementarity determining regions (CDRs) and framework regions. The CDRs (also termed hypervariable regions) are the regions within the VH and VL responsible for antibody binding.

The term "antibody" encompasses intact immunoglobulins, as well the variants and portions thereof, such as Fab fragments, Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker. In dsFvs the chains have been mutated to introduce a disulfide bond to stabilize the association of the chains. The term also includes genetically engineered forms such as chimeric antibodies, heteroconjugate antibodies (such as, bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997. The term also includes monoclonal antibodies (all antibody molecules have the same VH and VL sequences and therefore the same binding specificity) and polyclonal antisera (the antibodies vary in VH and VL sequence but all bind a particular antigen.)

Anti-proliferative activity: An activity of a molecule, for example a small molecule, an inhibitory RNA, and the like, which reduces proliferation of at least one cell type, but which may reduce the proliferation (either in absolute terms or in rate terms) of multiple different cell types (e.g., different cell lines, different species, etc.). In specific embodiments, the anti-proliferative activity of a small molecule, such as an inhibitor of ROS1 kinase will be apparent against cancer cells obtained from a subject that has aberrant ROS1 tyrosine kinase activity, including cells that have aberrant ROS1 activity and one or more mutations that render the cancer susceptible to cabozantinib and not to other tyrosine kinase inhibitors such as crizotinib.

Array: An arrangement of molecules, such as biological macromolecules (such as peptides or polynucleotide molecules) or biological samples (such as tissue sections), in addressable locations on or in a substrate. A "microarray" is an array that is miniaturized so as to require or be aided by microscopic examination for evaluation or analysis. In certain example arrays, one or more molecules (such as an antibody or peptide) will occur on the array a plurality of times (such as twice), for instance to provide internal controls. The number of addressable locations on the array can vary, for example from at least one, to at least 2, to at least 3, at least 4, at least 5, at least 6, at least 10, at least 20, at least 30, at least 50, at least 75, at least 100, at least 150, at least 200, at least 300, at least 500, least 550, at least 600, at least 800, at least 1000, at least 10,000, or more. In some examples, arrays include positive and/or negative controls, such as probes that bind housekeeping genes. In particular examples, an array includes polynucleotide molecules, such as oligonucleotide sequences that are at least 15 nucleotides in length, such as about 15-75 or 15-60 nucleotides in length. In particular examples, an array includes oligonucleotide probes or primers which can be used to detect nucleotides that encode tumor biomarker sequences (including RCC biomarkers). In an example, the array is a commercially available array such as Human Genome GeneChip® arrays from Affymetrix (Santa Clara, Calif.).

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays may be computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Biological signaling pathway: A systems of proteins, such as tyrosine kinases, and other molecules that act in an orchestrated fashion to mediate the response of a cell toward internal and external signals. In some examples, biological signaling pathways include tyrosine kinase proteins, such as ROS1, which can propagate signals in the pathway by selectively phosphorylating downstream substrates. In some examples a biological signaling pathway is disregulated and functions improperly, which can lead to aberrant signaling and in some instances hyper-proliferation of the cells with the aberrant signaling. In some examples, disregulation of a biological signaling pathway can result in a malignancy, such as cancer, for example the aberrant activation of a ROS1 kinase such as the formation of a fusion protein comprising ROS1 (including FIG-ROS and SLC-ROS). A ROS1 biological signaling pathway is a signaling pathway, in which ROS1 plays a role, for example by phosphorylation of downstream targets.

Biomarker: Molecular, biological or physical attributes that characterize a physiological or cellular state and that can be objectively measured to detect or define disease progression or predict or quantify therapeutic responses. A biomarker is a characteristic that is objectively measured and evaluated as an indicator of normal biologic processes, pathogenic processes, or pharmacologic responses to a therapeutic intervention. A biomarker may be any molecular structure produced by a cell or organism. A biomarker may be expressed inside any cell or tissue; accessible on the surface of a tissue or cell; structurally inherent to a cell or tissue such as a structural component, secreted by a cell or tissue, produced by the breakdown of a cell or tissue through processes such as necrosis, apoptosis or the like; or any combination of these. A biomarker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination.

A biomarker can be represented by the sequence of a polynucleotide from which it can be derived or any other chemical structure. Examples of such polynucleotides include miRNA, tRNA, siRNA, mRNA, cDNA, or genomic DNA sequences including any complimentary sequences thereof. One example of a biomarker is a DNA coding sequence for a protein comprising one or more mutations that cause amino acid substitutions in the protein sequence. Such a biomarker may be the coding sequence of a particular part of a protein such as the kinase domain of ROS1 comprising polynucleotide mutations that result in an amino acid substitution mutation in amino acid D2033 of SEQ ID NO: 1. In an exemplary embodiment, the mutation is a D2033N mutation.

Cancer: A disease or condition in which abnormal cells divide without control and are able to invade other tissues. Cancer cells spread to other body parts through the blood and lymphatic systems. Cancer is a term for many diseases. There are more than 100 different types of cancer in humans. Most cancers are named after the organ in which they originate. For instance, a cancer that begins in the colon may be called a colon cancer. However, the characteristics of a cancer, especially with regard to the sensitivity of the cancer to therapeutic compounds, are not limited to the organ in which the cancer originates. A cancer cell is any cell derived from any cancer, whether in vitro or in vivo.

Cancer is a malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc.

"Metastatic disease" or "metastasis" refers to cancer cells that have left the original tumor site and migrate to other parts of the body for example via the bloodstream or lymph system. The "pathology" of cancer includes all phenomena that compromise the wellbeing of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

Chemotherapeutic agent or Chemotherapy: Any chemical agent with therapeutic usefulness in the treatment of diseases characterized by abnormal cell growth. Such diseases include tumors, neoplasms, and cancer as well as diseases characterized by hyperplastic growth. In one embodiment, a chemotherapeutic agent is an agent of use in treating cancer, such as cancers characterized by aberrant ROS1 activity, including cancers characterized by aberrant ROS1 activity comprising mutations in the kinase domain of ROS1. Such agents include ROS1 inhibitors such as cabozantinib and crizotinib. Combination chemotherapy is the administration of more than one agent to treat cancer.

Contacting: Placement in direct physical association, including contacting of a solid with a solid, a liquid with a liquid, a liquid with a solid, or either a liquid or a solid with a cell or tissue, whether in vitro or in vivo. Contacting can occur in vitro with isolated cells or tissue or in vivo by administering to a subject.

Diagnostic: Identifying the presence or nature of a pathologic condition, such as, but not limited to cancer, such as cancer caused by aberrant ROS1 activity, including cancer caused by aberrant ROS1 activity that is insensitive to crizotinib and/or sensitive to cabozantinib. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis.

Domain: any part of polypeptide that can be demonstrated to mediate a particular protein function. For example, the kinase domain of human ROS1-CD74 fusion is from amino acid 1945 to amino acid 2222 in SEQ ID NO: 1 herein.

Effective amount: An amount of agent, such as a tyrosine kinase inhibitor that is sufficient to generate a desired response, such as reduce or eliminate a sign or symptom of a condition or disease, such as cancer, for example cancers expressing an aberrant ROS1 kinase. When administered to a subject, a dosage will generally be used that will achieve target tissue concentrations that has been shown to achieve anti proliferative activity in vitro. In some examples, an "effective amount" is one that treats (including prophylaxis) one or more symptoms and/or underlying causes of any of a disorder or disease, for example cancer, such as a cancer characterized by an aberrant ROS1 kinase. An effective amount can be a therapeutically effective amount, including an amount that prevents one or more signs or symptoms of a particular disease or condition from developing, such as one or more signs or symptoms associated with cancer.

Inhibitor: Any chemical compound, specific for a protein or other gene product that can directly interfere with the activity of a protein, such as a kinase, particularly a ROS1 kinase and more particularly a ROS1 kinase with aberrant activity. An inhibitor can inhibit the activity of a protein either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. Examples of inhibitors of aberrant ROS1 kinase domains include crizotinib and foretinib.

Inhibit: To reduce to a measurable extent, for example, to reduce activity (including aberrant activity) of a protein such as a kinase. In some examples, the kinase activity of a protein is inhibited, for example using a small molecule inhibitor of ROS1 such as crizotinib or foretinib.

Inhibiting or treating a disease: Inhibiting the full development of a disease or condition, for example, in a subject who has or who is at risk for a disease such cancer, for example, a cancer characterized by a ROS1 kinase with aberrant activity. "Treatment" refers to any therapeutic intervention that ameliorates a sign or symptom of a disease or pathological condition. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or wellbeing of the subject, or by other clinical or physiological parameters associated with a particular disease. A "prophylactic" treatment is a treatment administered to a subject who does not exhibit signs of a disease or exhibits only early signs for the purpose of decreasing the risk of developing pathology. A "therapeutic" treatment is a treatment administered after the development of significant signs or symptoms of the disease.

Kinase: An enzyme that catalyzes the transfer of a phosphate group from one molecule to another. Kinases play a role in the regulation of cell proliferation, differentiation, metabolism, migration, and survival. A "tyrosine kinase" transfers phosphate groups to a hydroxyl group of a tyrosine in a polypeptide. In some examples, a kinase is a ROS1 tyrosine kinase. Receptor protein tyrosine kinases (RTKs) contain a single polypeptide chain with a transmembrane segment. The extracellular end of this segment contains a high affinity ligand-binding domain, while the cytoplasmic end comprises the catalytic core and the regulatory sequences.

Non-receptor tyrosine kinases, such as ROS1, can be located in the cytoplasm as well as in the nucleus. They exhibit distinct kinase regulation, substrate phosphorylation, and function. A "preferential" inhibition of a kinase refers to an inhibitor that has the characteristic of inhibiting the activity of one kinase, such as ROS1, more it inhibits the activity of a second kinase, such as ALK or another tyrosine kinase.

Mass spectrometry: A method wherein, a sample is analyzed by generating gas phase ions from the sample, which are then separated according to their mass-to-charge ratio (m/z) and detected. Methods of generating gas phase ions from a sample include electrospray ionization (ESI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), Fourier-transform ion cyclotron resonance (FT-ICR) analyzers, and combinations thereof (for example, a quadrupole-time-of-flight analyzer, or Q-TOF analyzer). Prior to separation, the sample may be subjected to one or more dimensions of chromatographic separation, for example, one or more dimensions of liquid or size exclusion chromatography or gel-electrophoretic separation.

Mutation: A mutation is any difference in a polynucleotide or polypeptide sequence from a normal, consensus or "wild type" sequence. A mutant is any protein or polynucleotide sequence comprising a mutation. In addition a cell or an organism with a mutation may also be referred to as a mutant.

Some types of mutations include point mutations (differences in individual nucleotides or amino acids); silent mutations (differences in nucleotides that do not result in an amino acid changes); deletions (differences in which one or more nucleotides or amino acids are missing); frameshift mutations (differences in which deletion of a number of nucleotides indivisible by 3 results in an alteration of the amino acid sequence. Frameshift mutations may be described by the point at which the frameshift begins. A mutation that results in a difference in an amino acid may also be called an amino acid substitution mutation. Amino acid substitution mutations may be described by the amino acid change relative to wild type at a particular position in the amino acid sequence. Amino acid substitution mutations that result in a mutation from an amino acid residue to a stop codon (a protein truncation) can be described by identifying the residue which is mutated followed by an X. An example of such a mutation is a point mutation in D2033 of SEQ ID NO: 1 herein including a D2033N mutation (exemplified in SEQ ID NO: 2 herein).

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phospho-peptide or phospho-protein: A protein in which one or more phosphate moieties are covalently linked to one or more of the amino acids making up the peptide or protein. A peptide can be phosphorylated at multiple or single sites. Sometimes it is desirable for the phospho-protein to be phosphorylated at one site regardless of the presence of multiple potential phosphorylation sites. In vivo the transfer of a phosphate to a peptide is accomplished by a kinase. For example a tyrosine kinase such as ROS1 transfers a phosphate to a tyrosine residue of a substrate peptide or protein.

Polynucleotide: a nucleic acid polymer. A deoxyribonucleotide or ribonucleotide polymer including, without limitation, cDNA, mRNA, genomic DNA, methylated DNA, and synthetic (such as chemically synthesized) nucleic acids such as DNA, RNA, and/or methylated oligonucleotides. The polynucleotide molecule can be double-stranded or single-stranded. Where single-stranded, the nucleic acid molecule can be the sense strand or the antisense strand. In addition, nucleic acid molecule can be circular or linear. A polynucleotide molecule may also be termed a nucleic acid and the terms are used interchangeably.

Polypeptide: Any chain of amino acids, regardless of length or posttranslational modification (such as glycosylation, methylation, ubiquitination, phosphorylation, or the like). In one embodiment, a polypeptide is a ROS1-CD74 fusion polypeptide. "Polypeptide" is used interchangeably with "protein," and is used to refer to a polymer of amino acid residues. A "residue" refers to an amino acid or amino acid mimetic incorporated in a polypeptide by an amide bond or amide bond mimetic.

Sample: A sample, such as a biological sample, is a sample obtained from a plant or animal subject. As used herein, biological samples include all clinical samples useful for detection of mutations in tumor DNA, particularly mutations in the kinase domain of ROS1. Samples include, but not limited to, cells, tissues, and bodily fluids, including tissues that are, for example, unfixed, frozen, fixed in formalin and/or embedded in paraffin. In one example, a sample includes a tissue biopsy obtained from a subject with a tumor.

Sequence identity/similarity: The identity/similarity between two or more polynucleotide sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs BLASTP, BLASTN, BLASTX, TBLASTN and TBLASTX. Additional information can be found at the NCBI web site. BLASTN is used to compare polynucleotide sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a polynucleotide sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid or nucleotide sequences of greater than about 30 amino acids, the Blast 2 sequences function is employed using the default BLOSUM62 matrix set to default parameters, (gap existence cost of 11, and a per residue gap cost 5 of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein.

When aligning short peptides or polynucleotides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two polynucleotide molecules are closely related is that the two molecules hybridize to each other under stringent conditions, as described above. Polynucleotide sequences that do not show a high degree of identity may nevertheless encode identical or similar (conserved) amino acid sequences, due to the degeneracy of the genetic code. Changes in a polynucleotide sequence can be made using this degeneracy to produce multiple polynucleotide molecules that all encode substantially the same protein. An alternative (and not necessarily cumulative) indication that two polynucleotide sequences are substantially identical is that the polypeptide which the first polynucleotide encodes is immunologically cross reactive with the polypeptide encoded by the second polynucleotide.

One of skill in the art will appreciate that the particular sequence identity ranges are provided for guidance only; it is possible that strongly significant homologs could be obtained that fall outside the ranges provided.

Small molecule: A molecule, typically with a molecular weight less than 1000 Daltons or less than 500 Daltons, wherein the molecule is capable of modulating, to some measurable extent, an activity of a target molecule such as inhibiting the activity of a kinase, such as a ROS1 kinase with aberrant activity.

Subject: A living multicellular vertebrate organism, a category that includes, for example, mammals and birds. A "mammal" includes both human and non-human mammals, such as mice. In some examples, a subject is a patient, such as a patient diagnosed with cancer, particularly cancer characterized by a ROS1 kinase with aberrant activity, more particularly a cancer characterized by a ROS1 kinase with aberrant activity comprising one or more mutations in its kinase domain.

Substrate: A molecule that is acted upon by an enzyme, such as ROS1. A substrate binds with the enzyme's active site, and an enzyme-substrate complex is formed. In some examples, the enzyme catalyzes the incorporation of an atom or other molecule into the substrate, for example a kinase can incorporate a phosphate into the substrate, such as a peptide, thus forming a phospho-substrate.

Tissue: A plurality of functionally related cells. A tissue can be a suspension, a semi-solid, or solid. Tissue includes parts of organs collected from a subject such as the lung, the liver or a portion thereof.

Methods of Diagnosis

Disclosed herein are methods of diagnosing whether a subject has a cancer characterized by crizotinib resistance. In particular examples, the methods include identifying a mutation in SEQ ID NO: 3 herein that results in a D2033N mutation in SEQ ID NO: 1 alone or in combination with one or more additional mutations. The disclosed mutations can be identified by any suitable method known in the art. For example, they may be detected by any method of nucleic acid sequencing, through any method involving nucleic acid amplification, by any method of detecting a protein with one or more of the disclosed mutations, or any combination thereof. Examples of these methods are discussed in detail below.

In some embodiments, the mutation is detected in a biological sample obtained from the subject. Biological samples include cancer cells. For hematological malignancies, such biological samples can be taken from whole blood, from bone marrow aspirates, or any other source of tissue that could contain the hematological malignancy. Tumor samples can also include normal tissue. This normal tissue may serve as an internal negative control, especially in the case of assays that detect the presence of a biomarker in the context of tissue structure, including immunohistochemistry, FACS analysis, or in situ hybridization. It will appreciated by those of skill in the art that any method of obtaining tissue from a subject can be utilized, and that the selection of the method used will depend upon various factors such as the type of tissue, age of the subject, or procedures available to the practitioner.

Detecting Cancer Biomarkers

The disclosed mutation can be detected in a sample using any one of a number of methods well known in the art. Polynucleotides such as genomic DNA, particularly tumor genomic DNA can be isolated from a tumor sample, such as, in the case of a hematological malignancy, whole blood collected from a subject. General methods of polynucleotide isolation are well known to those of skill in the art. Such methods are disclosed in standard textbooks and handbooks of molecular biology and embodied in commercially available kits.

The mutations can be detected through nucleic acid sequencing. Sequencing may be performed on genomic DNA from the tumor through any method known in the art including Sanger sequencing, pyrosequencing, SOLiD® sequencing, massively parallel sequencing, barcoded sequencing, or any other sequencing method now known or yet to be disclosed. In Sanger Sequencing, a single-stranded DNA template, an oligonucleotide primer, a DNA polymerase, and nucleotides are used. A label, such as a radioactive label or a fluorescent label is conjugated to some of the nucleotides. One chain terminator base comprising a dideoxynucleotide (ddATP, ddGTP, ddCTP, or ddTTP, replaces the corresponding deoxynucleotide in each of four reactions. The products of the DNA polymerase reactions are electrophoresed and the sequence determined by comparing a gel with each of the four reactions. In another example of Sanger sequencing, each of the chain termination bases is labeled with a fluorescent label and each fluorescent label is of a different wavelength. This allows the polymerization reaction to be performed as a single reaction and enables greater automation of sequence reading.

In pyrosequencing, the addition of a base to a single stranded template to be sequenced by a polymerase results in the release of a pyrophosphate upon nucleotide incorporation. An ATP sulfyrlase enzyme converts pyrophosphate into ATP which in turn catalyzes the conversion of luciferin to oxyluciferin which results in the generation of visible light that is then detected by a camera.

In SOLiD® sequencing, the molecule to be sequenced is fragmented and used to prepare a population of clonal magnetic beads (in which each bead is conjugated to a plurality of copies of a single fragment) with an adaptor sequence. The beads are bound to a glass surface. Sequencing is then performed through 2-base encoding.

In massively parallel sequencing, randomly fragmented targeted DNA is attached to a surface through the use of an oligonucleotide adaptor. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

In pyrosequencing, massively parallel sequencing or SOLiD® sequencing, an artificial sequence called a barcode can be added to primers used to clone fragmented sequences or to adaptor sequences. A barcode is a 4-10 polynucleotide sequence that uniquely identifies a sequence as being derived from a particular sample. Barcoding of samples allows sequencing of multiple samples in a single sequencing run. (See Craig D W et al, *Nat Methods* 5, 887-893 (2008); incorporated by reference herein for descriptions and examples of barcodes.) DNA sequencing methods can, but need not, rely on nucleic acid amplification of a polynucleotide encoding a protein such as SEQ ID NO: 1.

Additional methods of detecting mutations in polynucleotides include detection through selective nucleic acid amplification of mutant sequences. An example of such a method is the amplification refractory mutation system (ARMS) Newton et al, *Nucleic Acids Res* 17, 2503-2515 (1989.) This method uses a primer that matches the nucleotide sequence immediately 5' of the mutation to be tested with the 3' end of the primer specific for the nucleotide sequence of the mutant. Such a primer will specifically amplify the mutant polynucleotide but not the wild type amino acid. Such reactions may be adapted to real-time PCR based systems such as TaqMan®. The disclosed mutations may also be identified using a microarray technique. Sequences corresponding to one or more of the disclosed mutants may be plated or arrayed on a microchip substrate. The arrayed sequences are then hybridized to isolated tumor genomic DNA. An array may also be a multi well plate.

The disclosed mutations may also be identified in proteins by, for example, mass spectrometry methodologies or antibody based methodologies that are designed to detect the difference between proteins that have the disclosed mutation and proteins that do not (such as the difference between SEQ ID NO: 1 and SEQ ID NO: 2 herein).

Methods of Treatment

Disclosed herein are methods of treating a cancer in a subject characterized by aberrant ROS1 activity. The methods include selecting a subject with a tumor, such as a subject with a tumor that is resistant to crizotinib. A sample is taken from the tumor and the tumor is subjected to conditions that allow the identification of a mutation that corresponds to a point mutation in D2033 of SEQ ID NO: 1, including a D2033N mutation (SEQ ID NO: 2). When the presence of the D2033 mutation is established, the subject is treated with cabozantinib.

The administration of the therapeutic agent can be for either a prophylactic or a therapeutic purpose. When provided prophylactically, the therapeutic agent is provided in advance of any symptom. The prophylactic administration of the compounds serves to prevent or ameliorate any subsequent disease process. When provided therapeutically, the therapeutic agent is provided at (or shortly after) the onset of a symptom of disease. For prophylactic and therapeutic purposes, the therapeutic agent can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition. One of skill in the art in light of this disclosure will be able to determine an effective dose of cabozantinib.

Examples of tumors that can be characterized by aberrant activity of ROS1 include: The tumor cell can be derived from any type of tumor from any species. Examples of types of tumors from which cells can be derived include Acute lymphoblastic leukemia; Acute myeloid leukemia; Adrenocortical carcinoma; AIDS-related cancers; AIDS-related lymphoma; Anal cancer; Appendix cancer; Astrocytoma, childhood cerebellar or cerebral; Basal cell carcinoma; Bile duct cancer, extrahepatic; Bladder cancer; Bone cancer, Osteosarcoma/Malignant fibrous histiocytoma; Brainstem glioma; Brain tumor; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/carcinoids; Burkitt lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/Malignant glioma, childhood; Cervical cancer; Childhood cancers; Chronic lymphocytic leukemia; Chronic myelogenous leukemia; Chronic myeloproliferative disorders; Colon Cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, Childhood; Extragonadal Germ cell tumor; Extrahepatic bile duct cancer; Eye Cancer, Intraocular melanoma; Eye Cancer, Retinoblastoma; Gallbladder cancer; Gastric (Stomach) cancer; Gastrointestinal Carcinoid Tumor; Gastrointestinal stromal tumor (GIST); Germ cell tumor: extracranial, extragonadal, or ovarian; Gestational trophoblastic tumor; Glioma of the brain stem; Glioma, Childhood Cerebral Astrocytoma; Glioma, Childhood Visual Pathway and Hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular Melanoma; Islet Cell Carcinoma (Endocrine Pancreas); Kaposi sarcoma; Kidney cancer (renal cell cancer); Laryngeal Cancer; Leukemias; Leukemia, acute lymphoblastic (also called acute lymphocytic leukemia); Leukemia, acute myeloid (also called acute myelogenous leukemia); Leukemia, chronic lymphocytic (also called chronic lymphocytic leukemia); Leukemia, chronic myelogenous (also called chronic myeloid leukemia); Leukemia, hairy cell; Lip and Oral Cavity Cancer; Liver Cancer (Primary); Lung Cancer, Non-Small Cell; Lung Cancer, Small Cell; Lymphomas; Lymphoma, AIDS-related; Lymphoma, Burkitt; Lymphoma, cutaneous T-Cell; Lymphoma, Hodgkin; Lymphomas, Non-Hodgkin (an old classification of all lymphomas except Hodgkin's); Lymphoma, Primary Central Nervous System; Marcus Whittle, Deadly Disease; Macroglobulinemia, Waldenström; Malignant Fibrous Histiocytoma of Bone/Osteosarcoma; Medulloblastoma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndrome, Childhood; Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple (Cancer of the Bone-Marrow); Myeloproliferative Disorders, Chronic; Nasal cavity and paranasal sinus cancer; Nasopharyngeal carcinoma; Neuroblastoma; Non-Hodgkin lymphoma; Non-small cell lung cancer; Oral Cancer; Oropharyngeal cancer; Osteosarcoma/malignant fibrous histiocytoma of bone; Ovarian cancer; Ovarian epithelial cancer (Surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sézary syndrome; Skin cancer (nonmelanoma); Skin cancer (melanoma); Skin carcinoma, Merkel cell; Small cell lung cancer; Small intestine cancer; Soft tissue sarcoma; Squamous cell carcinoma—see Skin cancer (nonmelanoma); Squamous neck cancer with occult primary, metastatic; Stomach cancer; Supratentorial primitive neuroectodermal tumor, childhood; T-Cell lymphoma, cutaneous (Mycosis Fungoides and Sézary syndrome); Testicular cancer; Throat cancer; Thymoma, childhood; Thymoma and Thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenström macroglobulinemia and Wilms tumor (kidney cancer).

Kits

A diagnostic kit may contain reagents such as oligonucleotides configured to perform nucleic acid amplification (including TaqMan® amplification) that specifically recognize mutant polynucleotides that cause amino acid changes such as amino acids in D2033 including D2033N. A diagnostic kit can also comprise an array that includes oligonucleotides that detect the disclosed mutations. A diagnostic kit can also contain a set of primers that amplify the kinase domain for sequencing or any other polynucleotide analysis. A diagnostic kit can also comprise antibodies specific for mutant forms of SEQ ID NO: 1, such as SEQ ID NO: 2.

EXAMPLES

The following examples are illustrative of the disclosed methods. In light of this disclosure, one of skill in the art will recognize that variations of these examples and other examples of the disclosed methods would be possible without undue experimentation.

Example 1

Molecular Profiling and Next-Generation Sequencing

Initial screening for a ROS1 fusion was performed via a dual-probe fluorescence in situ hybridization (FISH) break-apart test. On the basis of an upper level of split signals for break-apart probes (5' green probe and 3' red probe flanking the ROS1 kinase domain) on normal formalin-fixed paraffin-embedded tissue sections of approximately 5 μm, the cutoff for scoring the ROS1 FISH assay as positive for the presence of a rearrangement was set at 12% of cells with split signals or isolated 3' signals. Broad, hybrid-capture next-generation sequencing was performed using the MSK-IMPACT (Integrated Mutational Profiling of Actionable Cancer Targets) Illumina HiSeq 2500 platform (Cheng D T et al, J Mol Diagn 17, 251-264 (2015); incorporated by reference herein). A total of 341 cancer-related genes were interrogated, capturing base substitutions, small indels, copy number alterations, and select rearrangements. To detect somatic structural aberrations, a framework was developed that first aligns raw reads to the reference human genome (hg19) using the Burrows-Wheeler Alignment tool. Duplicates are then filtered using the Picard tools java package (samtools) and searched for candidate structural rearrangements using DELLY. All candidate somatic structural aberrations were filtered, annotated using in-house tools, and manually reviewed using the Integrative Genomics Viewer (IGV).

Example 2

Cabozantinib Administration

The patient received cabozantinib at a dose of 60 mg daily in 28-day cycles as part of an ongoing phase II clinical trial (NCT01639508) with an arm for ROS1-rearranged lung cancers. Inclusion criteria for patients in this trial were as follows: pathologic or cytologic evidence of non-small-cell lung cancer (NSCLC), clinical stage IV or recurrent/medically inoperable disease, a Karnofsky performance status of more than 70%, a life expectancy of more than 12 weeks, adequate hematologic, renal, and hepatic function, and measurable disease. Informed consent was obtained after the nature and possible consequences of the studies were explained. Treatment was discontinued in the event of disease progression, unacceptable toxicity, or patient withdrawal. Dose reductions were permitted as per a prescribed algorithm. Response was assessed using the Response Evaluation Criteria in Solid Tumors (RECIST) version 1.1 (Eisenhauer E A et al, Eur J Cancer 45, 228-247 (2009); incorporated by reference herein). Imaging was performed at baseline, 4 weeks, and every 8 weeks thereafter. In addition, scans to confirm response were performed as per RECIST. The primary endpoint of the trial was objective response. Secondary endpoints included progression-free survival and overall survival.

Example 3

Cell Culture

Parental Ba/F3 cells (American Type Culture Collection, ATCC) were cultured in complete medium (RPMI medium 1640 with 10% (vol/vol) FBS, L-glutamine, penicillin/streptomycin) supplemented with 15% (vol/vol) WEHI-3-conditioned media as a source of IL-3. CD74-ROS1D2033N was generated using site-directed mutagenesis by following manufacturer's protocol (Agilent). Ba/F3 cells were maintained at densities of $0.5\text{-}1.5 \times 10^6$ cells/mL and infected with retrovirus encoding native or mutant versions of human CD74-ROS1. GFP-based selection of transduced cells was performed with a FACSAria cell sorter (BD Biosciences). Stable cell lines were washed with complete medium to remove IL-3. Cells that grew out after IL-3 withdrawal were maintained in complete medium and used for in vitro assays.

Example 4

Apoptosis Measurement

Ba/F3 cells expressing native CD74-ROS1 or CD74-ROS1D2033N were treated with 1, 10, and 100 nM crizotinib or cabozantinib for 72 h. The Guava Nexin Assay Kit (EMD/Millipore) was used to detect apoptosis according to the manufacturer's protocol. Annexin V62 positive cells were counted using a Guava easyCyte flow cytometer (Millipore).

Example 5

Cell Growth/Viability Assays

Inhibitors were prepared as 1 mM stocks in DMSO prior to each experiment. Inhibitors were distributed at 2× concentration using a D300 Digital Dispenser (Hewlett Packard) capable of accurately administering very small volumes (10 pL-150 nL) into 384-well plates pre-loaded with 25 μL/well of complete medium. Ba/F3 cells expressing CD74-ROS1 constructs were seeded (800 cells/well; 25 μL) into drug plates using a Multidrop Combi Reagent Dispenser (Thermo Scientific), and plates were incubated for 72 h at 37° C., 5% CO2. Viability was measured using a methanethiosulfonate (MTS)-based assay (CellTiter96 Aqueous One Solution; Promega) read on a Biotek Synergy 2 plate reader. Proliferation experiments were performed three independent times in triplicate. Data were normalized using Microsoft Excel, and 50% and 90% growth inhibitory concentration ($IC_{50}$ and $IC_{90}$) values were calculated with GraphPad Prism software using a non-linear curve fit equation modified using previously described parameters (Sebaugh J L, Pharm Stat 10, 128-134 (2011); incorporated by reference herein).

Example 5

Immunoblot Analysis

Ba/F3 CD74-ROS1 and CD74-ROS1D2033N 74 cells were treated with the indicated concentrations of inhibitors for 2 h, pelleted, washed once in ice-cold PBS, and lysed in 200 µL of cell lysis buffer (Cell Signaling Technology) that was supplemented with 0.25% deoxycholate, 0.05% SDS, and protease and phosphatase inhibitors. Equal amounts of protein were extracted with SDS sample buffer for 15 min at 80° C. and resolved on 4-15% Tris-glycine or 4-12% Bis-Tris precast gels (Criterion; Bio-Rad). Proteins transferred to Immobilon-FL membranes (Millipore) were probed with: phospho-ROS1 [Cell Signaling Technology (CST); 3078, 1:1000], total ROS1 (CST; 3266, 1:1000), phospho-ERK1/2 (CST; 9101, 1:1000), total ERK2 (Santa Cruz; sc-1647, 1:2000), phospho-AKT (CST; 4060, 1:1000), AKT (BD Transduction Laboratories; 610860, 1:1000), pSHP2 (CST; 3703), pSTAT3 (CST, 9131), and GAPDH (Ambion; AM4300, 1:5000). Blots were imaged using either a LI-COR Odyssey imaging system or the Bio-Rad ChemiDoc imaging station according to the manufacturer's protocol for immunoblot detection with use of Infrared dye or horseradish peroxidase-conjugated secondary antibodies, respectively.

Example 6

Molecular Models of Native ROS1 and ROS1D2033N

The crystal structure of the active conformation of the ROS1 kinase domain in complex with crizotinib was used for structural studies (PDB entry 3ZBF) (7); however, missing residues in the P-loop and A-loop were modeled using Schrödinger Suite (version 3.1; Schrödinger, LLC) and hydrogen atoms were added. The ROS1D2033N structure was generated using the native ROS1 crystal structure, by single amino-acid substitution. In the absence of a crystal structure for the inactive conformation of ROS1 kinase, a homology-based model was generated. Using the Prime module of Schrödinger's package, a knowledge-based model was built for both native ROS1 and ROS1D2033N. The crystal structure of ALK (PDB entry 4FNY) (Epstein L F et al, J Biol Chem 287, 37447-37457 (2012); incorporated by reference herein) in the inactive state was used as a structural template (sequence homology~64%) to build inactive ROS1. All four systems (ROS1 and ROS1D2033N in both the active and inactive states) were solvated using a pre-equilibrated TIP3P water-box (Jorgensen W L et al, J Chem Phys 79, 926 (1983); incorporated by reference herein) maintaining a distance of 20 Å from any protein atom to the edge of the box. Compatible sodium and chloride ions were added to neutralize the simulated systems (Joung I S and Cheatham T E, J Phys Chem B 112, 9020-9041 (2008); incorporated by reference herein). The final orthorhombic box contained a total of 68,758-72,236 atoms.

Example 7

Ensemble Docking

Ensemble docking was performed using the Glide program of Schrödinger's package (Suite 2012: Maestro, version 9.3). 500 conformations were extracted from each system simulated (one conformation for every nanosecond) and a docking grid for the receptor was generated using the binding site residues (L1951, A1978, K1980, E1997, M2001, L2028, G2032, L2086, and D2102). Ligands (crizotinib and cabozantinib) were prepared using the Ligprep module of the Schrödinger's package (version 3), docked using the GlideXP method (Glide version 5.8; Schrödinger, LLC), and analyzed for binding interactions (Friesner R A et al, J Med Chem 49, 6177-6196 (2006); incorporated by reference herein). The most favorable docking score computed using the ensemble docking was reported.

Example 8

Molecular Dynamics Simulations

Molecular dynamics (MD) simulations were performed using the Amber ff12SB force field (Maier J A et al, J Chem Theor Comput 11, 3696-3713 (2015); incorporated by reference herein) in the NAMD simulation software (Phillips J C et al, J Comput Chem 26, 1781-1802 (2005); incorporated by reference herein). All hydrogen atoms were restrained using the SHAKE algorithm (Miyamoto S and Kollman P A, J Comput Chem 13, 952-962 (1992); incorporated by reference herein). Periodic boundary conditions with particle mesh Ewald (PME) summation were employed to handle the long-range electrostatic interactions (real-space truncation at 9.0 Å and grid spacing of 1.0 Å) (Darden T et al, J Chem Phys 98, 10089 (1993); incorporated by reference herein). Temperature and pressure were controlled at 300 K and 1 atm using the Nose'-Hoover Langevin piston algorithm (Martyna G J et al, J Chem Phys 101, 4177 (1994); incorporated by reference herein) and Langevin dynamics (Pastor R W et al, Mol Phys 65, 1409-1419 (1988); incorporated by reference herein), respectively. All four systems were simulated for 500 ns and coordinates were saved every 10 ps for further conformational analysis. The CPPTRAJ software of the AmberTools suite was used for post processing of the MD generated trajectories (Roe D R et al, J Chem Theory Comput 9, 3084-3095 (2013); incorporated by reference herein). Electrostatic potential surface representation of native ROS1 and ROS1D2033N was generated using Adaptive Poisson-Boltzmann Software (Baker N A et al, Proc Natl Acad Sci USA 98, 10037-10041 (2001); incorporated by reference herein).

Example 9

Discovery of the ROS1 D2033N Mutation and Response to Cabozantinib in the Setting of Acquired Resistance to Crizotinib A 50 year-old female never smoker with metastatic lung adenocarcinoma involving the pleura received three cycles of first-line systemic therapy with cisplatin, pemetrexed, and bevacizumab (FIG. 1, FIG. 9). Rearrangement of ROS1 was detected via fluorescence in situ hybridization (FISH) and confirmed by sequencing using MSK-IMPACT, a validated broad, hybrid-capture next-generation sequencing (NGS) test, as an in-frame fusion of CD74 (exons 1-6) with ROS1 (exons 34-42) in the diagnostic biopsy sample. The patient was treated with crizotinib (250 mg twice daily), achieving a durable partial response (64% reduction in disease burden via RECIST v1.1). At 18 months, she underwent whole brain radiation for new brain metastases. Disease control outside the brain was maintained on crizotinib.

Figure 2:
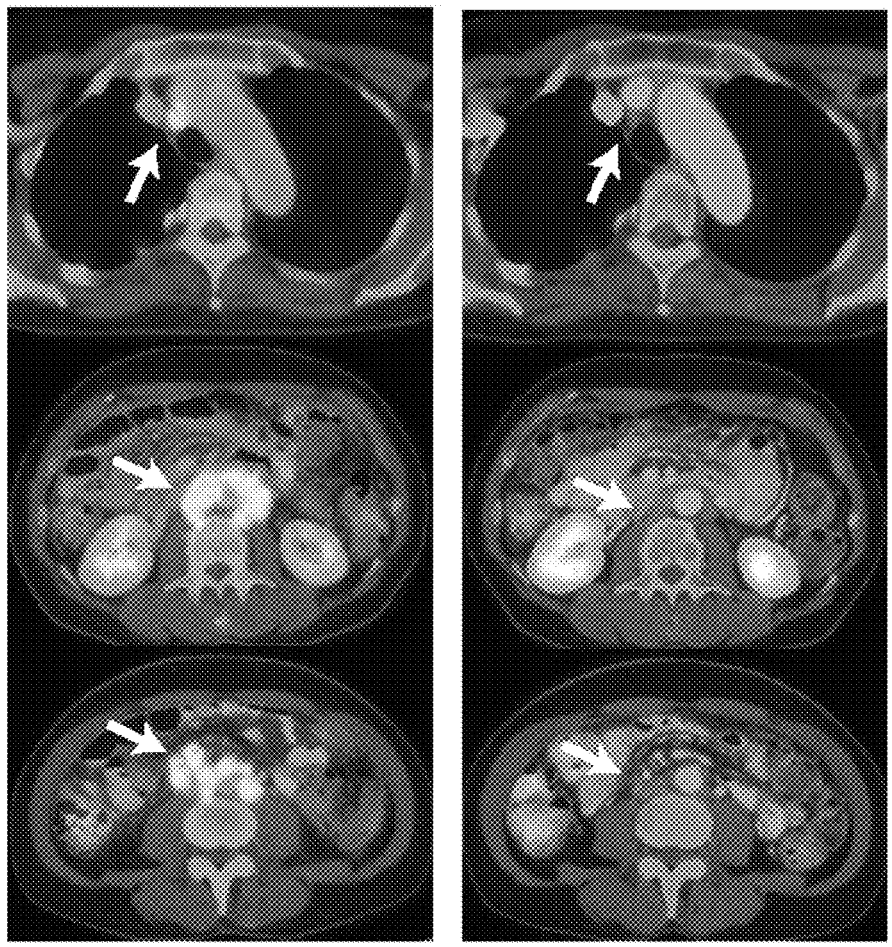
FIG. 2 shows radiographic evidence of clinical response to cabozantinib. Left panel: Fused CT/PET images demonstrating disease progression at the onset of acquired resistance to crizotinib and prior to cabozantinib treatment. Growing hypermetabolic mediastinal and retroperitoneal adenopathy are indicated by white arrows. Right panel: Fused CT/PET images obtained 4 weeks after the initiation of cabozantinib showing rapid resolution of hypermetabolic mediastinal and abdominopelvic lymph nodes.

After a total of 26 months on crizotinib, the patient developed widespread disease progression. Computed and positron emission tomography (CT/PET) identified new bilateral pulmonary nodules, mediastinal and retroperitoneal adenopathy, and peritoneal carcinomatosis (FIG. 2, left panel). To identify molecular mechanism(s) of crizotinib-resistance, a biopsy was collected from a growing retroperitoneal lymph node after progression on crizotinib and analyzed using NGS that confirmed persistent expression of the CD74-ROS1 rearrangement (FIG. 1). This deep-sequencing also revealed the acquisition of a mutation—ROS1 D2033N (c.6097G>A)—that resides within the ROS1 kinase domain (FIG. 1) and was not detected in the pre-crizotinib diagnostic sample from this patient.

Of 644 sequencing reads over that specific region of ROS1 that were at 663× depth, the variant frequency of c.6097G>A was 14% in the crizotinib-resistant tumor specimen and undetectable the matched normal peripheral blood control. Additional morphologic assessment of tumor content as well as FISH analysis shows that the tumor content was 60-70% and the CD74-ROS1 fusion was identified in 70% of the cells analyzed. This suggests that the acquired D2033N mutation is subclonal and present in about 20-23% of the tumor cells that harbor the CD74-ROS1 fusions. While these data strongly suggest that ROS1 D2033N is a novel acquired crizotinib-resistant mutation, though it is possible that a very rare population (frequency <2%) was present in the pre-crizotinib treatment sample that was below the detection threshold of NGS platform used here. Given clinical resistance to crizotinib, the ROS1 inhibitor cabozantinib was initiated (60 mg daily) on a phase II clinical trial (NCT01639508). Partial response was rapidly achieved by 4 weeks, and confirmed at 8 weeks (FIG. 2, right panel). At 12 weeks, a near complete response was achieved with a 92% reduction in disease burden. The patient remains on therapy approaching 8 months (FIG. 1).

Example 10

Figure 3A:
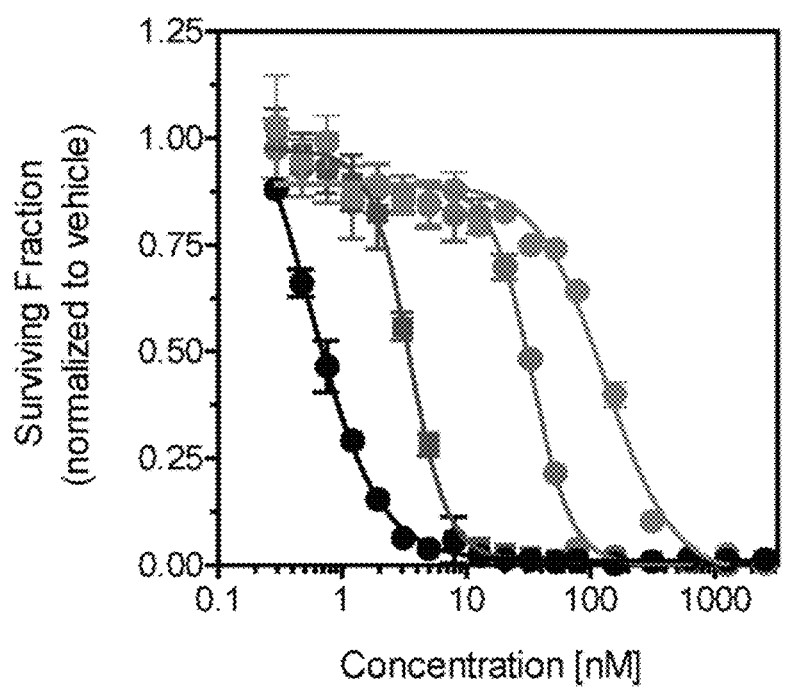
FIG. 3A is a graph showing cell growth and viability of Ba/F3 cells expressing native CD74-ROS1 or CD74-ROS1 D2033N after 72 h exposure to crizotinib and cabozantinib. Results are shown as mean viability normalized to vehicle-treated control±SEM (n=4). Concentrations that decreased cell viability by 50 or 90% are listed as $IC_{50}$ and $IC_{90}$, respectively.
Figure 3B:
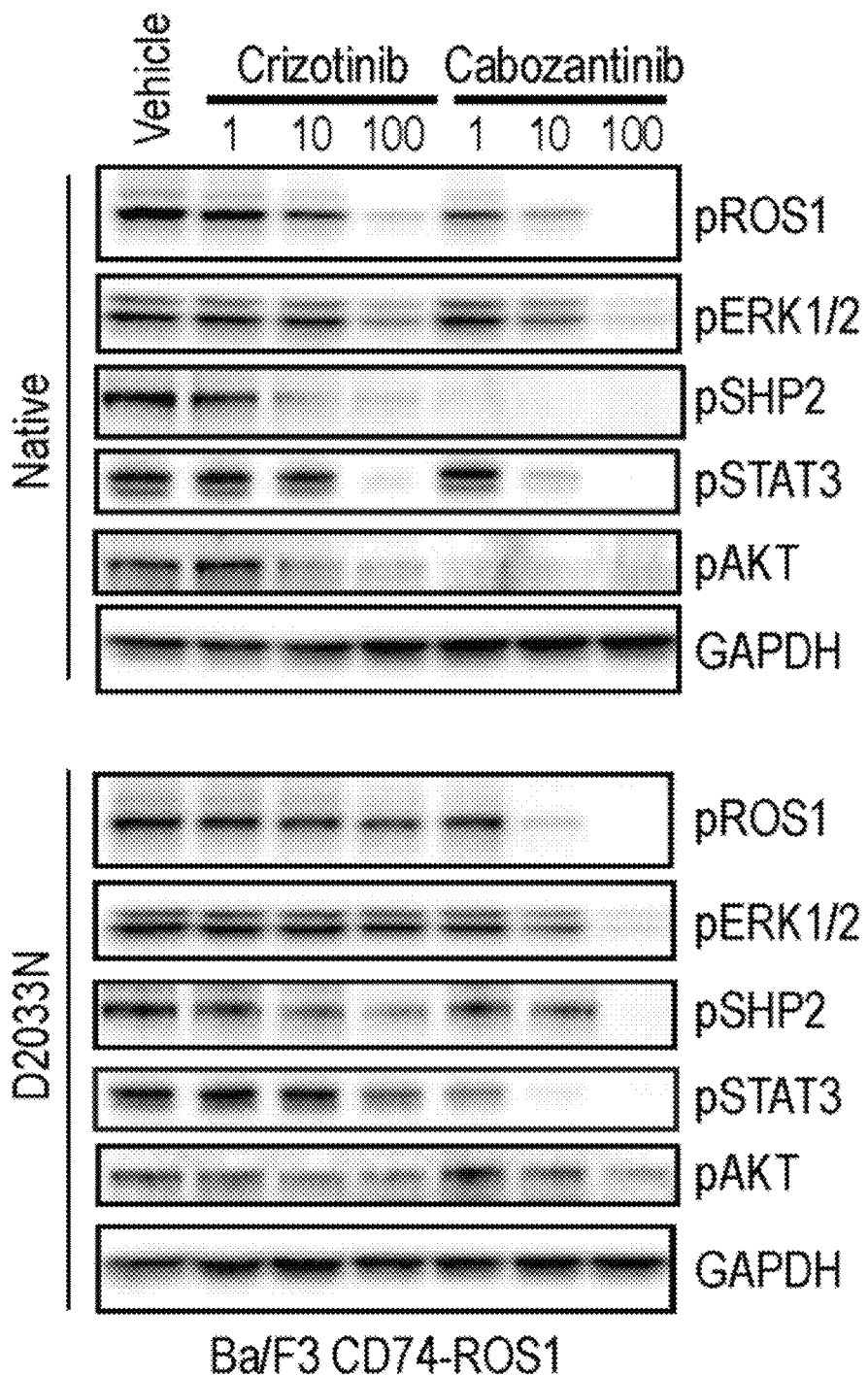
FIG. 3B is an image of the results of an immunoblot analysis of ROS1, ERK1/2, SHP2, STAT3 and AKT phosphorylation from Ba/F3 CD74-ROS1 and CD74-ROS1D2033N cells after treatment with the indicated concentrations of crizotinib and cabozantinib. GAPDH expression is included as a loading control.
Figure 5A:
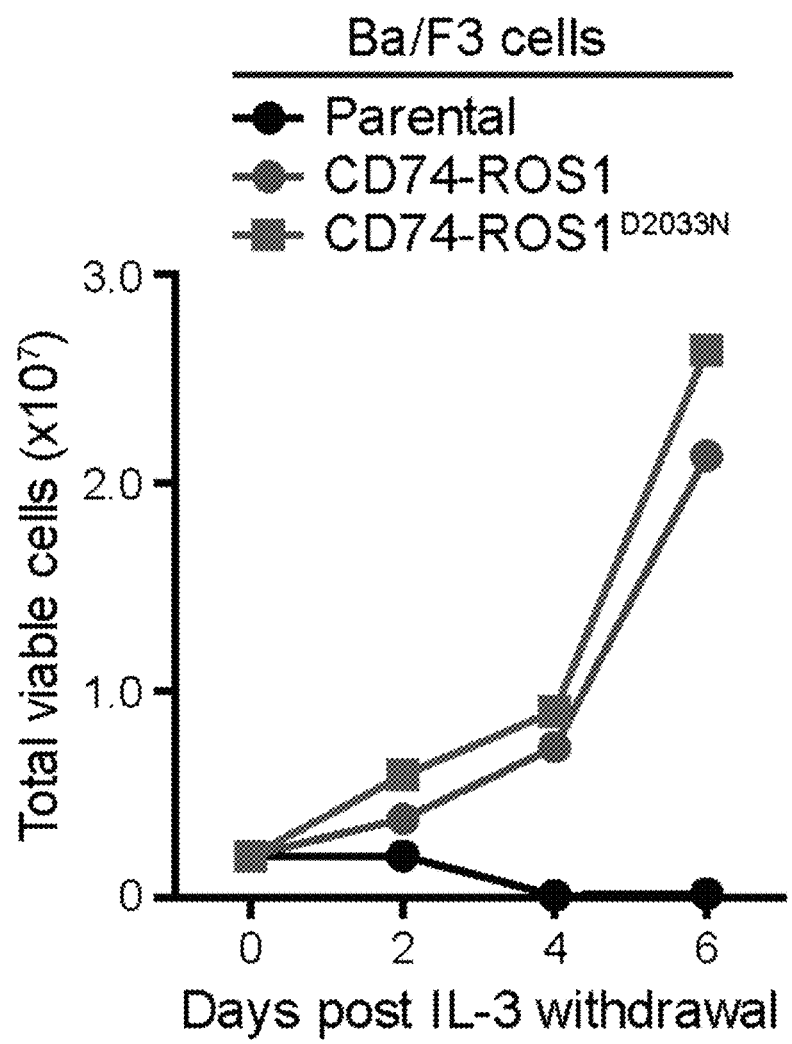
FIG. 5A is a plot of an IL-3 withdrawal assay for Ba/F3 cells retrovirally transduced with native CD74-ROS1 or CD74-ROS1D2033N. Total viable cell number was determined by counting cells on days 2, 4, and 6 after removal of IL-3 from the culture medium.
Figure 5B:
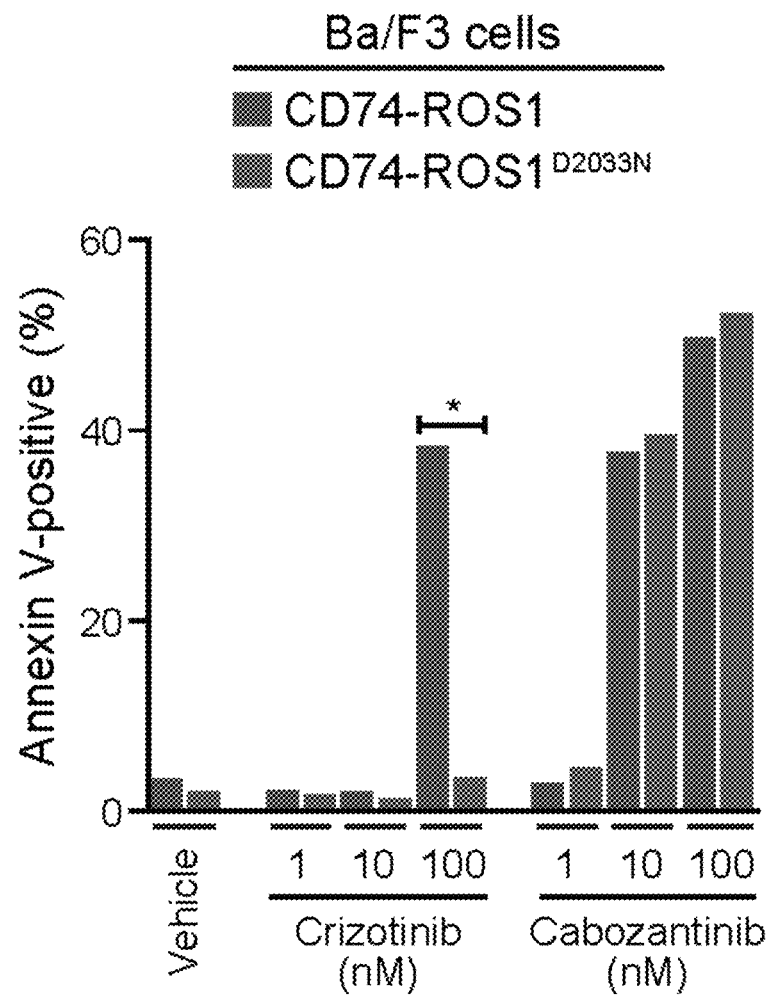
FIG. 5B is a graph showing apoptosis induction in Ba/F3 CD74-ROS1 and CD74-ROS1 D2033N cells after 72 h of inhibitor treatment at the indicated concentrations. Percentage of cells that were Annexin V-positive after inhibitor treatment is indicated as % Apoptotic. 2,000 cells were counted per condition.
Figures 6, 7:
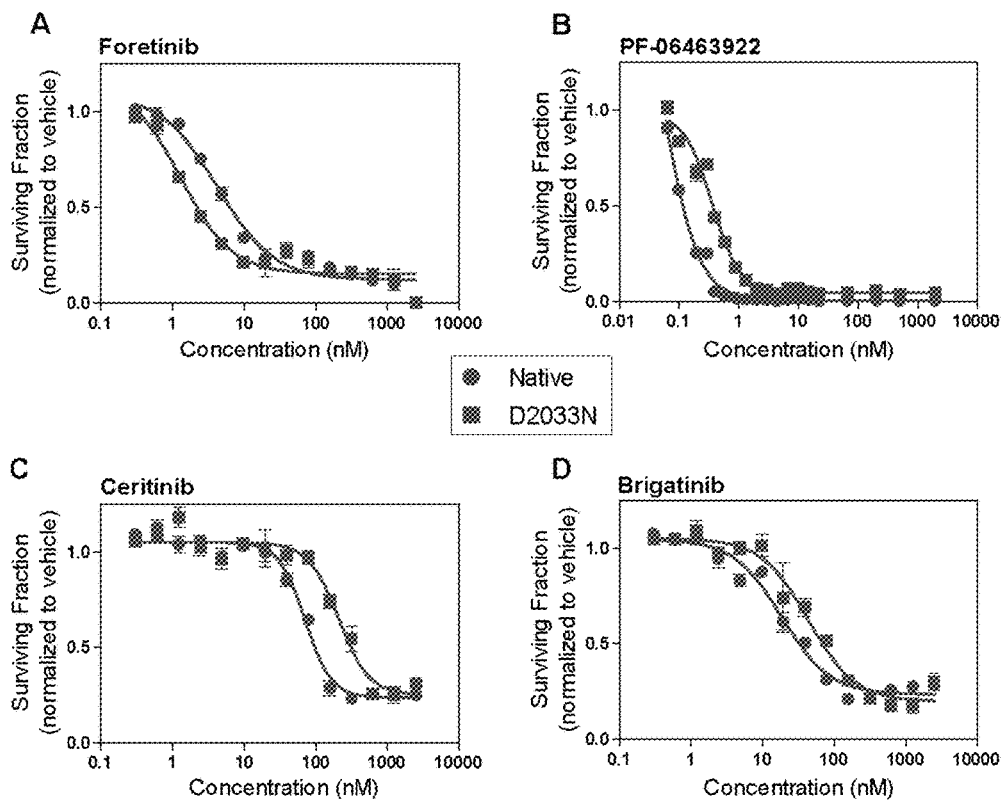
FIG. 6 is a set of four plots showing Sensitivity of CD74-ROS1D2033N to a spectrum of ROS1 kinase inhibitors. Cell growth and viability of Ba/F3 cells expressing native CD74-ROS1 or CD74-ROS1D2033N after 72 h exposure to foretinib (Panel A), PF-06463922 (Panel B), ceritinib (Panel C), and brigatinib (Panel D). Results are shown as mean viability normalized to vehicle-treated control±SEM (n=3 to 6).
FIG. 7 is a table listing inhibitor IC50 (nM) for native versus ROS1D2033N mutant.
Figure 8:
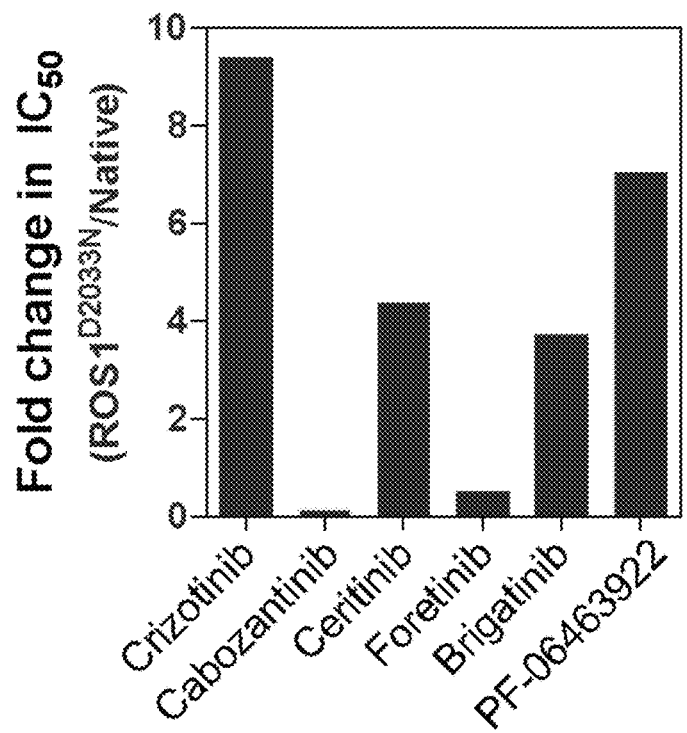
FIG. 8 is a graph depicting the fold increase in $IC_{50}$ (nM) for Ba/F3 cells expressing CD74-ROS1 D2033N compared to native CD74-ROS1.
Figure 10:
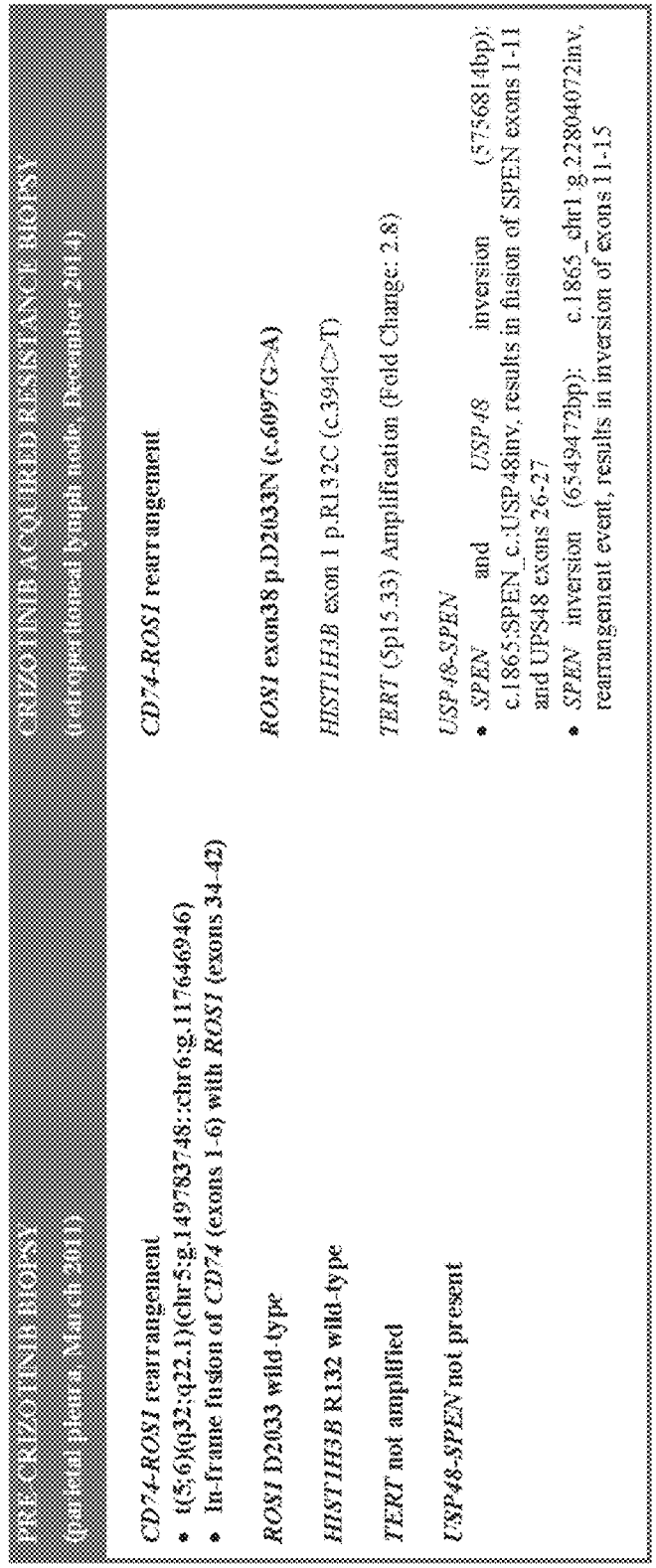
FIG. 10 is a description of mutations seen pre- and post crizotinib treatment of the patient treated as described in FIG. 9 indicating acquired crizotinib resistant mutations.

Functional Assessment of Crizotinib and Cabozantinib Sensitivity Against the CD74-ROS1D2033N Mutant in Cell-Based Assays To assess the role of the CD74-ROS1D2033N mutation as a causative mechanism for crizotinib-resistance, cell-based sensitivity profiling was performed using Ba/F3 cells transformed with native CD74-ROS1 or CD74-ROS1D2033N (FIG. 5A). Ba/F3 cells are an interleukin-3-dependent pro-B murine cell line that is a well-established model system for eliciting oncogene addiction and testing kinase inhibitor efficacy (Warmuth M et al, Curr Opin Oncol 19, 55-60 (2007); incorporated by reference herein). During interleukin-3 withdrawal of Ba/F3 cells, CD74-ROS1 and CD74-ROS1D2033N conferred comparable capacity for and kinetics of outgrowth in the absence of the requisite cytokine, suggesting that the mutation does not provide a fitness or growth advantage (FIG. 5A). However, while crizotinib exhibited markedly reduced growth inhibition of Ba/F3 CD74-ROS1D2033N cells as compared to native CD74-ROS1 cells ($IC_{50}$: 132.3 versus 21.4 nM, respectively; FIG. 3A), cabozantinib potently inhibited the growth of both native and D2033N mutant CD74-ROS1 cells ($IC_{50}$: 0.78 versus 2.8 nM, respectively). Inhibition of Ba/F3 CD74-ROS1 D2033N cells by cabozantinib was consistent with induction of apoptotic cell death (FIG. 5B). Immunoblot assessment following short-term treatment of native CD74-ROS1 cells with crizotinib or cabozantinib showed dose-dependent inhibition of phosphorylation of ROS1 and its downstream effectors SHP2, ERK1/2, AKT and STAT3 (FIG. 3B). However, in CD74-ROS1D2033N cells, only treatment with cabozantinib suppressed ROS1 activation and downstream signaling (FIG. 3B). To characterize the spectrum of inhibitor sensitivity of CD74-ROS1D2033N, the sensitivity of this mutant to a panel of other ROS1 kinase inhibitors was also assessed (FIG. 6). As compared to cells expressing native CD74-ROS1, the CD74-ROS1D2033N mutant conferred 4.3-, 3.7- and 7-fold decrease in sensitivity to ceritinib, brigatinib, and PF-06463922, respectively, but remained highly sensitive to foretinib, a close structural analog of cabozantinib (FIGS. 7 and 8). Furthermore, although the sensitivity of CD74-ROS1D2033N to PF-06463922 was reduced seven fold, due to high potency of this recently described heterocyclic ROS1 inhibitor (FIGS. 6 and 7) (Zou H Y et al, Proc Natl Acad Sci USA 112, 3493-3498 (2015); incorporated by reference herein), the CD74-ROS1D2033N mutant is still inhibited in the low nanomolar range in vitro.

Example 11

Figure 4A:
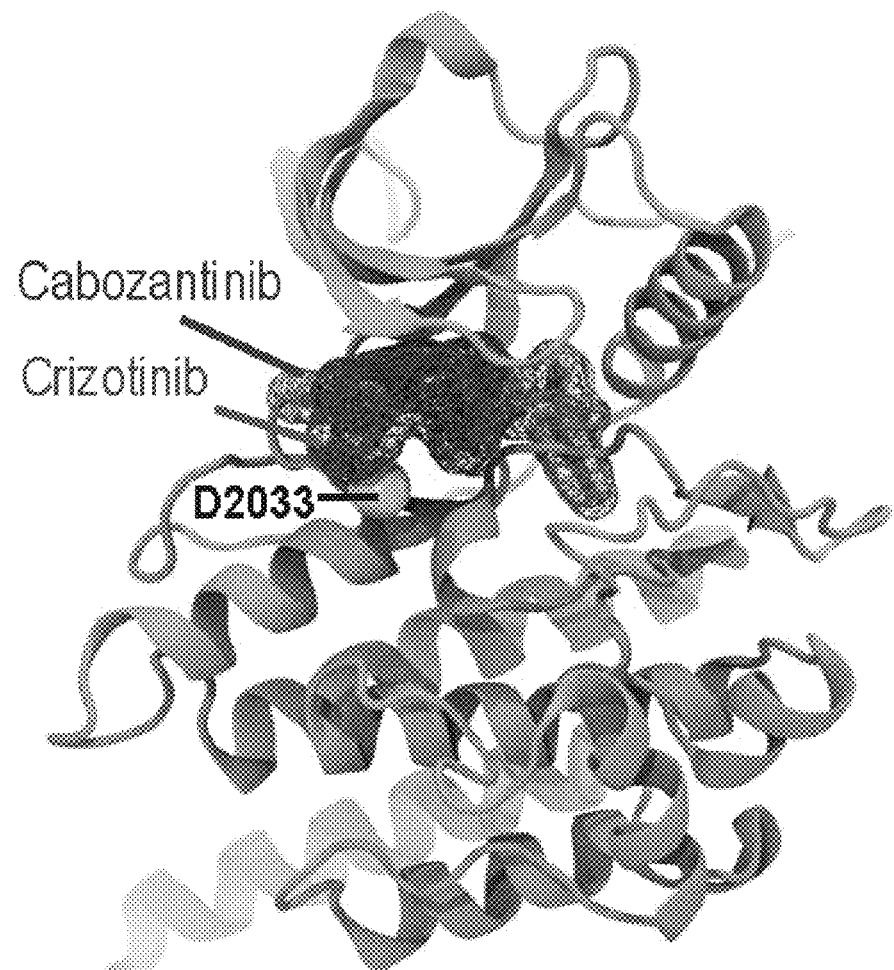
FIG. 4A shows the structure of the native ROS1 kinase shown as a cartoon model. Crizotinib (red) and cabozantinib (green) binding regions are highlighted using mesh surfaces and residue D2033 is shown as a yellow sphere.

Structural Differences in the Binding Requirements of Crizotinib and Cabozantinib Underlie Inhibitor Resistance Versus Sensitivity To further understand the resistance and selectivity imparted by the D2033N mutation, molecular dynamics (MD) simulation of the native and mutant ROS1 kinase domains were performed using the available X-ray crystal structure (7) and docking analysis of inhibitors on the MD-generated ensemble (FIG. 4A). Both the native ROS1 and ROS1D2033N systems were stable during the 500 ns MD simulation and displayed a similar conformation of the ATP-binding site. ROS1 D2033N showed slight reduction in the flexibility of the P-loop compared to native ROS1, possibly due to reorienting of the carbonyl moiety of P-loop residue L1951, which is necessary to participate in a water mediated hydrogen bond with N2033.

Figure 4B:
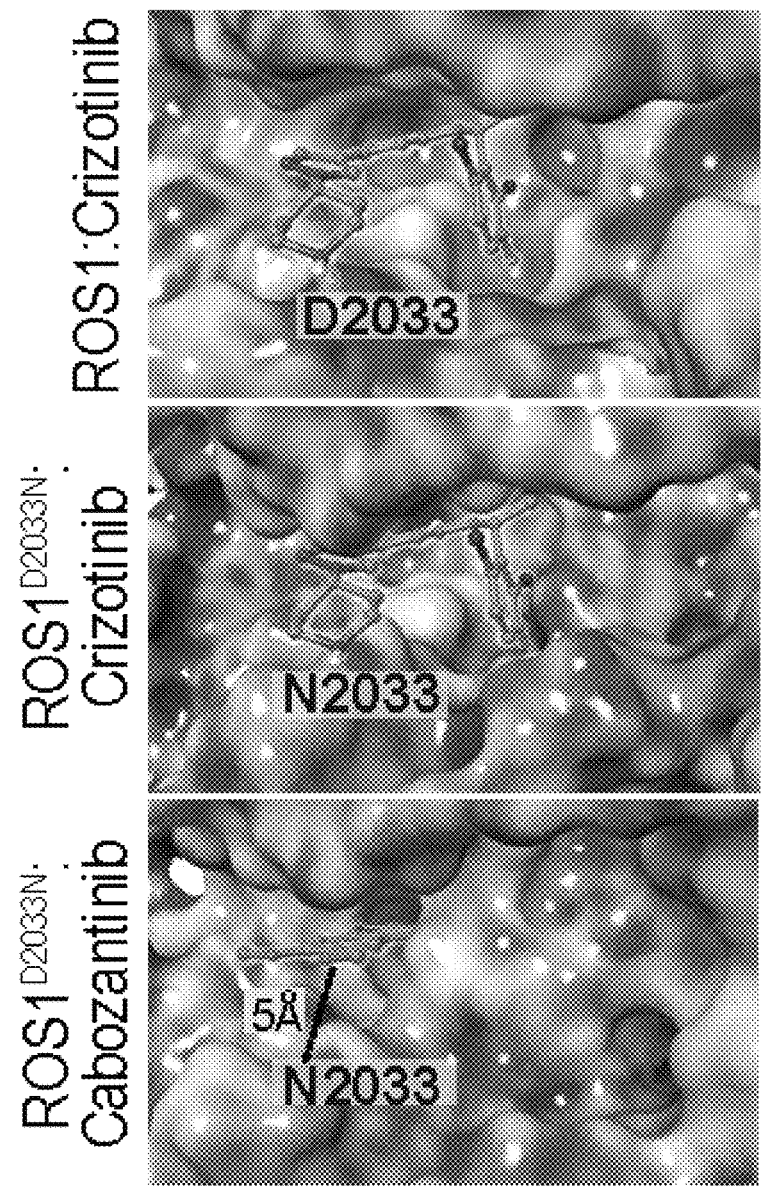
FIG. 4B shows the surface representation of inhibitor docking to native and mutant ROS1. Surfaces are colored according to electrostatic potential (negatively charged region as red and positively charged region as blue). The position and identity of residue 2033 is highlighted, and the indicated inhibitor is shown using a licorice model (green). Top panel: Crizotinib bound to native ROS1. Middle panel: Hypothetical model of crizotinib binding to ROS1D2033N based on protein alignment. Bottom panel: Cabozantinib bound to ROS1D2033N based on docking simulations.

More dramatically, the D2033N mutation dictates a major change in the electrostatic potential at the exterior surface of the ATP-binding site. Docking analysis performed on the native ROS1 ensemble revealed a strong electrostatic interaction between the protonated piperidine moiety of crizotinib and the negatively charged D2033 residue (FIG. 4B, top panel). This key interaction is lost as a result of the D2033N mutation, which lacks the negatively charged functional group optimally positioned to interact with this region of bound crizotinib. This mutation also induced subtle reorientations of neighboring residues that further hindered favorable interaction with the protonated piperidine region of crizotinib.

Hypothetical placement of crizotinib on the ROS1D2033N mutant (based on structural alignment) indicated electrostatic repulsion between the positively charged piperidine nitrogen and the amine group of N2033 (FIG. 4B, middle panel). In contrast, the nearest portion of the cabozantinib binding site was at least 5 Å away from residue 2033 in both native ROS1 and ROS1D2033N, and its binding does not involve interaction with this residue in either case (FIG. 4B, bottom panel). Consistently, comparatively poorer docking scores were observed for crizotinib for the ROS1D2033N mutant versus native ROS1 (−7 kcal/mol and −9.6 kcal/mol, respectively; lower scores indicate stronger inhibitor binding), whereas favorable and comparable docking scores were seen for cabozantinib bound to ROS1D2033N and native ROS1 (−10 and −12 kcal/mol, respectively).

Figures 4C, 4D:
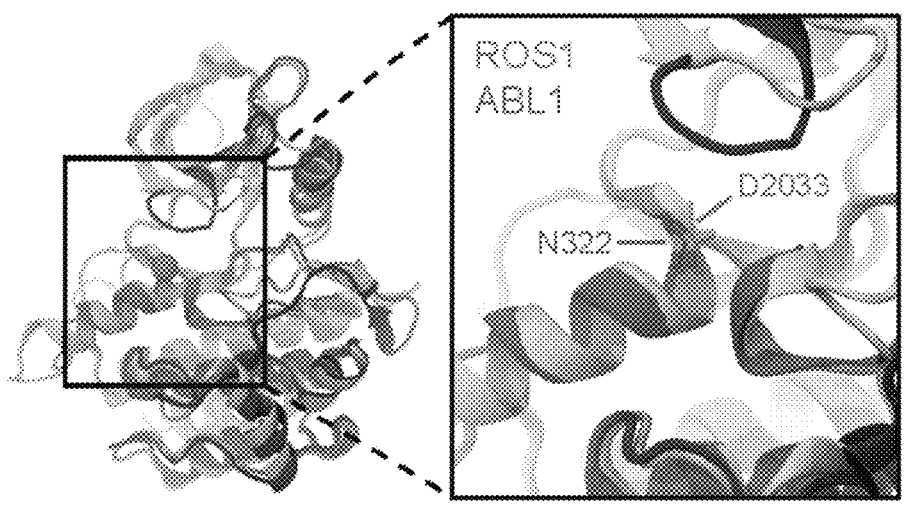
FIG. 4C shows the protein alignment of human ROS1 paralogs and select additional kinases implicated in cancer. A focused window surrounding position 2033 of ROS1 is shown with the analogous position and identity indicated for each protein.
FIG. 4D shows the structural alignment of the active conformations of the ROS1 and ABL1 kinase domains. The crystal structures of active ROS1 and ABL1 are show superimposed in cartoon ribbon format. Position D2033 in ROS1 (red ball) and the analogous position in ABL1 (N322; blue ball) are highlighted for reference.

Homology alignment suggests that the native aspartate at position 2033 of ROS1 is highly conserved among ROS1 paralogs, although significant variability is seen among other less closely related kinases (FIG. 4C). Interestingly, the analogous position in ABL1 kinase (322) is an asparagine, thus phylogenetically mimicking the ROS1 D2033N mutation. Although structural modeling shows similarity in the active conformations of the ROS1 and ABL1 kinase domains, docking simulations suggest that the lack of productive electrostatic interaction may contribute to crizotinib's selectivity for ROS1 over ABL1 (Cui J J et al, J Med Chem 54, 6342-6363 (2011); incorporated by reference herein) (FIG. 4D).

ROS1 D2033N is a mechanism of acquired resistance to crizotinib therapy in ROS1-rearranged lung cancer. The D2033N mutation occurs at the solvent-front region of the ATP211 binding site of ROS1, similar to G2032R, the only other acquired resistance mutation that has been identified in a patient to date (Song A et al, Clin Cancer Res 21, 2379-2387 (2015); incorporated by reference herein). As follow-up of ROS1-rearranged lung cancer patients treated with crizotinib is still relatively short, subsequent sequencing analysis of larger cohorts of crizotinib-resistant patients will be required to better establish the spectrum and frequency of mutations such as D2033N. While the analogous mutation in the highly related ALK kinase (D1203N) has not been reported in clinical crizotinib resistance in ALK-rearranged lung cancer, it was detected in a cell-based in vitro screen for resistance to crizotinib (Heuckmann J M et al, Clin Cancer Res 17, 7394-7401 (2011); incorporated by reference herein). While second-generation ROS1 inhibitors are effective in vitro against select ROS1 kinase domain mutations identified from cell-based resistance screens, including those at the gatekeeper position, mutations arising in the solvent-front region are resistant to several of these agents (Katayama R et al, Clin Cancer Res 21, 166-174 (2015); incorporated by reference herein). Identifying ROS1 inhibitors that are active in this setting is thus crucial, and as shown here, can have a substantial impact on clinical outcome.

This mutation confers high-level resistance to crizotinib in vitro, compromising drug binding secondary to a major change in electrostatic interaction and reorientation of neighboring residues. Cabozantinib overcomes acquired resistance to crizotinib mediated by the ROS1 D2033N mutation, inducing downstream pathway inhibition and apoptotic cell death. While in vitro characterization suggests a potentially slightly increased sensitivity of the D2033N mutant to cabozantinib relative to native CD74-ROS1, expanded structural studies would be required to interrogate such subtle changes in IC50. Structural modeling does suggest accommodation of this mutation by cabozantinib binding, corroborating previous data showing that cabozantinib is likewise active against the ROS1 G2032R mutant (Davare M A et al, Proc Natl Acad Sci USA 112, E5381-E5390 (2015); incorporated by reference herein), and implying a role for this compound in circumventing crizotinib-resistant solvent-front mutations.

While the CD74-ROS1D2033N mutation was detected as subclonal population in the patient under study, the rapid and near complete tumor response to the more potent ROS1 inhibitor cabozantinib (92% reduction in 12 weeks) combined with in vitro cell-based and structural validation experiments strongly implicate it as the dominant mechanism of crizotinib-resistance in this patient. The evidence for clinical resistance in the setting of only a subclonal resistant cell population is not surprising, as a similar scenario is common, for example, to the development of the well-characterized secondary EGFR T790M resistance mutation in non-small cell lung carcinoma patients harboring a sensitizing mutation and treated with EGFR inhibitors (Ohashi K et al, J Clin Oncol 31, 1070-1080 (2013) and Ladanyi M and Pao W, Mod Pathol 21 Suppl 2, S16-S22 (2008); both of which are incorporated by reference herein). These mutations are often found in only small proportion of the tumor cells, yet result in profound acquired resistance in patients.

Importantly, this report represents the first clinical description of a dramatic response to ROS1-directed targeted therapy in the setting of acquired resistance to crizotinib. While pre-clinical validation experiments strongly suggest that the dramatic clinical response to cabozantinib is due to potent inhibitory activity against the acquired CD74-ROS1 D2033N mutation. These findings highlight the growing need to further characterize mechanisms of acquired resistance to ROS1 TKI therapy in a systematic fashion, at the level of structural and functional validation as well as in the clinic. Many of these studies are ongoing and are likely to inform clinical practice in the future. A prospective phase 2 trial of cabozantinib with a cohort for ROS1-rearranged lung cancer continues to enroll patients (NCT01639508).

The invention claimed is:

1. A method of treating a subject with a non-small cell lung cancer tumor characterized by a CD74-ROS1 fusion, the method comprising:
receiving a sample comprising a portion of the solid tumor from the subject;
amplifying a nucleic acid fragment comprising bases 6295-6297 from SEQ ID NO: 3 from the sample, and
detecting an amino acid substitution mutation in bases 6295-6297 of SEQ ID NO: 3 in the amplified nucleic acid fragment, wherein the mutation results in a D2033N amino acid substitution of SEQ ID NO: 1, and
administering a therapeutically effective amount of cabozantinib to the subject, thereby treating the subject.

2. The method of claim 1 where the nucleic acid fragment comprises nucleotides 6287-6305 of SEQ ID NO: 3.

3. The method of claim 1 comprising sequencing the nucleic acid fragment using Sanger sequencing.

4. The method of claim 1 further comprising isolating tumor genomic DNA or tumor messenger RNA from the sample prior to amplification.

5. The method of claim 1 further comprising obtaining the sample from the subject.

6. The method of claim 1 further comprising detecting the ROS-1 fusion prior to amplifying the nucleic acid fragment by fluorescent in situ hybridization or nucleic acid sequencing.

7. The method of claim 1 where the non-small cell lung cancer is resistant to crizotinib.

8. A method of treating a subject with non-small cell lung cancer characterized by a CD74-ROS1 fusion, the method comprising:
receiving a sample from the subject, where the sample comprises isolated tumor genomic DNA or isolated tumor messenger RNA;
amplifying a nucleic acid fragment comprising bases 6295-6297 of SEQ ID NO: 3 from the sample;
detecting an amino acid substitution mutation in bases 6295-6297 of SEQ ID NO: 3 in the amplified nucleic acid fragment, wherein the mutation results in a D2033N amino acid substitution of SEQ ID NO: 1;
and administering a therapeutically effective amount of cabozantinib to the subject, thereby treating the subject.

9. The method of claim 8 where the nucleic acid fragment comprises nucleotides 6287-6305 of SEQ ID NO: 3.

10. The method of claim 8 comprising sequencing the nucleic acid fragment using Sanger sequencing.

11. The method of claim 8 where the non-small cell lung cancer is resistant to crizotinib.

* * * * *